United States Patent
Pfeifer

(10) Patent No.: US 12,296,160 B2
(45) Date of Patent: May 13, 2025

(54) ELECTRO-STIMULATION DEVICE AND METHOD OF SYSTEMATICALLY COMPOUNDED MODULATION OF CURRENT INTENSITY WITH OTHER OUTPUT PARAMETERS FOR AFFECTING BIOLOGICAL MATERIALS

(71) Applicant: FAST TRACK TECHNOLOGIES, INC., Newport Beach, CA (US)

(72) Inventor: Geoffrey Pfeifer, Ojai, CA (US)

(73) Assignee: FAST TRACK TECHNOLOGIES, INC., Newport Beach, CA (US)

( * ) Notice: Subject to any disclaimer, the term of this patent is extended or adjusted under 35 U.S.C. 154(b) by 1059 days.

(21) Appl. No.: 17/077,961

(22) Filed: Oct. 22, 2020

(65) Prior Publication Data
US 2021/0038879 A1     Feb. 11, 2021

Related U.S. Application Data

(63) Continuation-in-part of application No. 16/038,127, filed on Jul. 17, 2018, now abandoned, which is a continuation-in-part of application No. 14/776,944, filed as application No. PCT/US2014/029963 on Mar. 15, 2014, now Pat. No. 10,022,541.

(Continued)

(51) Int. Cl.
| | |
|---|---|
| A61N 1/04 | (2006.01) |
| A61N 1/20 | (2006.01) |
| A61N 1/36 | (2006.01) |
| A61N 1/372 | (2006.01) |
| C12M 1/42 | (2006.01) |
| C12N 13/00 | (2006.01) |

(52) U.S. Cl.
CPC ......... *A61N 1/0404* (2013.01); *A61N 1/0484* (2013.01); *A61N 1/205* (2013.01); *A61N 1/36034* (2017.08); *A61N 1/36062* (2017.08); *A61N 1/36121* (2013.01); *A61N 1/36128* (2013.01); *A61N 1/36135* (2013.01); *A61N 1/372* (2013.01); *C12M 35/02* (2013.01); *C12N 13/00* (2013.01)

(58) Field of Classification Search
CPC .. A61N 1/0484; A61N 1/205; A61N 1/36034; C12N 13/00
See application file for complete search history.

(56) References Cited

U.S. PATENT DOCUMENTS

| | | | | |
|---|---|---|---|---|
| 10,022,541 | B2 * | 7/2018 | Pfeifer | A61N 1/326 |
| 2007/0299895 | A1 * | 12/2007 | Johnson | G06F 1/0321 |
| | | | | 708/270 |
| 2009/0082829 | A1 * | 3/2009 | Panken | A61N 1/36139 |
| | | | | 607/45 |

* cited by examiner

*Primary Examiner* — Tammie K Marlen
*Assistant Examiner* — Maria Catherine Anthony
(74) *Attorney, Agent, or Firm* — Jonathan Kidney; Intelink Law Group, P.C.

(57) ABSTRACT

An electro-therapy device that generates a mixed electrical signal through electrodes, wherein the mixed electrical signal is a combination of at least two different frequencies, a first frequency having a first minimum and maximum microamp range and a second frequency having a different second minimum and maximum microamp range. The higher of the two frequencies is superimposed on the lower frequency, (Continued)

creating a current intensity window as an envelope along a profile of the lower frequency. The mixed electrical signal is automatically applied for a pre-determined period of time, and amplitude and/or duration and/or frequencies is varied according to a pre-set schedule.

20 Claims, 15 Drawing Sheets

Related U.S. Application Data

(60) Provisional application No. 61/787,900, filed on Mar. 15, 2013.

ELECTRO-STIMULATION DEVICE AND METHOD OF SYSTEMATICALLY COMPOUNDED MODULATION OF CURRENT INTENSITY WITH OTHER OUTPUT PARAMETERS FOR AFFECTING BIOLOGICAL MATERIALS

CROSS-REFERENCE TO RELATED APPLICATIONS

This application is a Continuation patent application of and claims priority to U.S. patent application Ser. No. 16/038,127, filed Jul. 17, 2018, which claims priority to U.S. patent application Ser. No. 14/776,944 filed Sep. 15, 2015, now issued as U.S. Pat. No. 10,022,541 on Jul. 17, 2018, which is a 371 of PCT Application No. PCT/US2014/029963, filed Mar. 15, 2014, which claims priority and the benefit of U.S. Provisional Patent Application No. 61/787,900, filed Mar. 15, 2013, the contents of which are hereby incorporated by reference in their entirety. All of these patent applications have the same inventors as this application.

FIELD

This invention relates to electro-stimulation schemes for treatment of biological tissue. More particularly, it relates to low to no supervision methods and approaches for specially modulated electro-stimulation of tissue and cell and the accompanying support environment.

BACKGROUND

Clinical electrotherapy devices have been used for over a century to treat many types of medical problems. During the past several decades, Transcutaneous Electrical Nerve Stimulation (TENS) has been used successfully as an alternative or adjunct to drugs for the symptomatic relief and management of pain syndromes. Typically, TENS devices temporarily block pain sensations by providing a milliampere level electrical signal that interferes with the ability of the affected nerves to transmit the pain signals to the brain. A problem with this electrical stimulation is the process known as habituation, accommodation or tachyphylaxis. Essentially, with increasing duration of TENS pain treatment approaches, the stimulated nerves become habituated to the electrical current, diminishing treatment efficacy. While TENS is known to block pain, it is not known to promote tissue healing.

Microcurrent Electrical Nerve Stimulation (MENS) therapy, which is at lower microampere levels, has shown tissue healing effects. However, the suite of MENS devices on the market have very specific restrictions on their abilities. For example, limited number of frequencies, a limited range of current intensities, some with timers, waveform/polarity limitations, and so forth. All of these prior art systems involve detailed setup and require active "during-treatment" control and adjustment.

Accordingly, there has been a long-standing need in the electro-treatment industry for devices and/or methods to address these and other shortcomings in the prior art.

SUMMARY

The following presents a simplified summary in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

In one aspect of the disclosed embodiments, a method to therapeutically aid tissue or biological material via direct application of a mixed electrical signal is provided, comprising: placing at least one or more electrodes in contact with at least one of a subject tissue, biological material, and a supporting environment; initiating a triggering of the mixed electrical signal; automatically applying, via processor control, a frequency dependent mixed electrical signal through the one or more electrodes, wherein the mixed electrical signal is a combination of at least two different frequency signals, a first frequency signal having a first minimum and maximum microamp range and a second frequency signal having a different second minimum and maximum microamp range, wherein a higher of the two frequency signals is superimposed on the lower of the two different frequency signals, whereby a current intensity window is sustained as an envelope along a profile of the lower of the two different frequency signals; and maintaining the application of the mixed electrical signal for a pre-determined period of time and varying the mixed electrical signal's amplitude and/or duration and/or frequencies according to a programmed schedule.

In another aspect of the disclosed embodiments, the above method is described further comprising adding a fixed or varying DC offset to the mixed electrical signal, wherein the DC offset can be positive or negative in value; and/or wherein the electrodes are connected to an electrode pad; and/or wherein the pad is disposable; and/or wherein at least one of a peak amplitude and frequency of the first frequency is varied; and/or wherein at least one of a peak amplitude and frequency of the second frequency is varied; and/or wherein at least one of a peak amplitude and frequency of the second frequency is varied; and/or wherein the electrodes are subcutaneous to the subject tissue; and/or wherein method is applied to a human or animal for at least one of spinal, intracranial, anti-inflammatory, immunomodulatory, neuromodulatory, musculo-skeletal, and visceral effects; and/or wherein the method is applied to a human or animal to activate or deactivate opioid receptors and up-down-regulate the opioid and endorphin systems as a bio-electronic medicine alternative to opioids or drug withdrawal; and/or further comprising multi-well cell culture plates, wherein the method is applied to at least one of a microbiological, plant and animal cell in the plates; and/or wherein the method is applied to a human or animal to influence at least one of epigenetic function, histone acetylation, histone deacetylation, DNA methylation, elastin formation, collagen formation, and connective tissue growth; and/or wherein the method is applied to a human or animal to influence at least one of external cell membrane receptor(s), nuclear cell membrane receptor(s), agonist, antagonist, inverse agonist, calcium ion transport, sodium ion transport, and potassium ion transport; and/or wherein the method is applied in vitro or in vivo to influence at least one of cell signaling, cell-to-cell communication, intracellular charge, extracellular charge, functioning of intracellular organelles, mitochondrial functioning, protein synthesis, phases of mitosis, interstitial fluid fields, and lymphatic functions; and/or further comprising placing the electrodes in a plant soil or support environment, to influence at least one of disease process, infection, water consumption, soil microbiology, soil fertility, and nutrient uptake; and/or wherein the method is applied to at least one of a head, ear, transcranially, and specific nerves to affect aspects of brain function; and/or the method is applied in vitro or in vivo to produce at least one of an anti-inflammatory effect, immunomodulation effect, cytokine expression, Th1 to Th2 immune expression, immune complement system, anti-viral effects, and anti-bacterial effect; and/or wherein the method is applied to a human or animal in at least one of intravaginally, bladder, prostate, rectum, bone, organ, skin, limb, mouth, gum, sinus, ear, nose, and throat; and/or wherein the electrodes are disposed in an ingestible pill, to treat at least one of irritable bowel syndrome, colitis, ulcerative colitis, gastroesophageal reflux disorder, diverticulitis, Crohn's disease, celiac disease, gallstone pain, gastroparesis, dysbiosis, food poisoning, diarrhea, and constipation; and/or wherein the method is used in vitro or in vivo to affect at least one of cellular electrophysiological feedback, cellular functions, cellular photosensors, and biophoton emissions.

In yet another aspect of the disclosed embodiments, a device to therapeutically aid tissue or biological material via direct application of a mixed electrical signal is provided, comprising: a strip of stretchable material wearable, either via adhesion to a skin or wrapping around the skin; one or more electrodes disposed on a surface of the strip; and a controller dispensing an electrical signal through the one or more electrodes, wherein the electrical signal is a combination of at least two different frequency signals, a first frequency signal having a first minimum and maximum microamp range and a second frequency signal having a different second minimum and maximum microamp range, wherein a higher of the two frequency signals is superimposed on the lower of the two different frequency signals, whereby a current intensity window is sustained as an envelope along a profile of the lower of the two different frequency signals, wherein the mixed electrical signal is applied for a pre-determined period of time and the mixed electrical signal's amplitude and/or duration and/or frequencies is varied according to a programmed schedule, to provide therapeutic benefits to the user.

In yet another aspect of the disclosed embodiments, an apparatus to aid or discourage growth of biological material via direct application of a mixed electrical signal is provided, comprising: a container with a consumable medium and growing organism therein; one or more electrodes internal to the container and in contact with the medium; a controller dispensing an electrical signal through the one or more electrodes, wherein the electrical signal is a combination of at least two different frequency signals, a first frequency signal having a first minimum and maximum microamp range and a second frequency signal having a different second minimum and maximum microamp range, wherein a higher of the two frequency signals is superimposed on the lower of the two different frequency signals, whereby a current intensity window is sustained as an envelope along a profile of the lower of the two different frequency signals, wherein the mixed electrical signal is applied for a pre-determined period of time and the mixed electrical signal's amplitude and/or duration and/or frequencies is varied according to a programmed schedule, to promote or retard at least one of a longevity of the consumable medium and growing organism.

In yet another aspect of the disclosed embodiments, the above apparatus is provided, wherein the consumable medium is beer, wine, kombucha, or yogurt.

DETAILED DESCRIPTION

Figure 1:
FIG. 1 is an illustration of a self-enclosed embodiment on the back of a horse.

Electrotherapy devices of the related art are limited to blocking pain, promoting healing of dermal wounds, non-healing bone fractures, disease of the macula, and exercising and/or massaging muscles or dispersing lymphedema. For example, Cheng et al., Arch. Dermatol., Vol. 129, pp. 264-271 (1993), reported an experiment involving the conducting of electrical currents through rat skin submerged in a buffer to study the effect of electric current on glycine incorporation into proteins and on the alpha-aminoisobutyric acid uptake by skin cells. Constant currents from 100 to 600 microamperes were used during incubation of the rat skin in solution for a period of up to four hours at 37 degrees Centigrade. It was reported that, at this low current, the synthesis of ATP was increased. However, at currents over 800 microamperes, that effect was lost.

Wood et al., Arch. Dermatol., 129, pp. 999-1008 (1993), reported the treatment of decubitus ulcers using pulsed, low-intensity direct current ("PLIDC"). A PLIDC instrument (MEMS CS 600, Harbor Medical Inc., Minneapolis, Minn.), an investigational exempt device, was used with a 12 volt battery to provide current breakthrough across the ulcer of 300 microamperes followed by treatment at 600 microamperes. The current was pulsed starting negative with a frequency of about 0.8 Hz.

A variety of U.S. patents (e.g. U.S. Pat. Nos. 2,622,601, 2,771,554) involve TENS devices that vary the rate, amplitude or pulse width of the generated electrical pulse in a singular way. Typically, accommodation would still occur unless an individual manually adjusted the controls extensively during the treatment. The process was mentally and physically demanding and no one can accurately and quickly adjust manual controls in a manner that taps the potential maximum pain relief provided by non-user controlled means. For example, U.S. Pat. No. 4,019,519 (Geerling) discloses a unit having only its amplitude adjustable. U.S.

Pat. No. 4,084,595 (Miller), and U.S. Pat. No. 4,759,368 (Spanton) disclose TENS devices in which the stimulus signal has a manually and independently varied rate, amplitude and pulse width. To provide improved output pulse compensation, one TENS device (U.S. Pat. No. 5,184,617 to Harris et al.) provided manual adjustment of pulse width control linked to a predetermined change in range of intensity of the pulses. Although various types of programmed and manual variation enabled one to deal with accommodation, pain relief in milliamperage TENS devices is a function of the relationship between the strength of the current intensity and the duration of that impulse. The relationship when plotted graphically is known as a strength-duration curve. U.S. Pat. No. 2,808,826 (Reiner), disclosed a unit that permitted instantaneous changes in pulse width and amplitude to two pre-set points along the strength-duration curve. U.S. Pat. Nos. 4,340,063, 4,431,002 and 4,442,839 (Maurer), disclose units with modulation of amplitude, pulse width, and repetition rates, but the problem of accommodation still existed.

MENS therapy has recently been shown to have other beneficial effects that go beyond TENS pain blocking theories. MENS has been shown to have significant effects on diminishing inflammation and edema as well as positive effects on collagen and cellular ATP promotion. However, these benefits are limited by the therapeutic concepts utilized by those doing the programming of the electrical output capabilities of the devices available today, the amount of time that a practitioner can monitor the application of therapy as well as the number of times this limited therapy can be repeated. For instance, the process of repairing microtraumas in the periosteum and bone of equine bucked shins cannot only be attributed to the anti-inflammatory effect reported in the literature with certain forms of microcurrent, for if that was the case treatment with strong veterinary anti-inflammatory medications would be adequate primary therapy. Anti-inflammatory therapies are used adjunctively in bucked shins, but are not known to heal the damaged tissues.

Despite the above breath of knowledge in this field, none of the above contemplate an embodiment for a therapeutic technique of modulating the current intensity function as a waveform being driven between two systematically changing maximum and minimum microamperage values while simultaneously carrying a systematically changing DC or AC frequency among other modulatable output parameters in a single or multi-channel system. The application of this method has been demonstrated by the inventor as not only providing pain relief, but also in healing of human and animal tissues; and reveals an electrotherapeutic technique of compounding the biophysical effects of combined waveforms. Moreover, the inventor has discovered the specific combination of signals used in his technique has shown remarkable cellular influence providing, for example, specific modulation of a myriad of micro-cellular level activities and indicates treatment for cell membrane receptor(s), channels, DNA process regulation, mitochondrial functioning, cell-to-cell communication, growth stimulation and so forth. Further macro-cellular effects have been demonstrated, for example, in one or more of the following: stimulation/retardation of tissue healing, tissue perfusion, lymphatic functioning, neurotransmitter, opioid receptor/mood control, tumor control, allegories, blood transport stimulation, viral, inflammation, and so forth.

In view of the limitations in the prior art, both in current waveform type and application methodology, a specially modulated low current intensity, microcurrent electrical therapy design is described. For example, one embodiment has a programmable device producing a standardized therapeutic sequence and dosage of electrotherapy with resultant increase in reliability of results. Further, various embodiments for non-wire lead based electro-therapy are described. For example, another embodiment has a miniaturized device mounted directly to an electrode (of a multitude of designs) without wires thereby facilitating usability in both human and animal applications.

The mechanism of action produced by the therapeutic techniques disclosed herein is hypothesized to be due to one or more of the following: increased perfusion and/or vasodilation secondary to nitric oxide induction; enhancement of stem cell attraction, and/or migration, and/or implantation, and/or stem cell induction, etc.; anti-inflammatory effect due to modulation of cytokines, neuropeptides and other pro-inflammatory substances; anti-edema effect due to regulation of intracellular water and ion balance vs. extracellular water and ionic balance; regulation of cellular physiologic balance (e.g. between osteoclasts and osteoblasts in bone formation), systemic and local hormone and peptide release as well as cell-to-cell messenger signaling systems and activation of cell membrane proteins by electrical means, hence the potential to influence gene activation through this cell membrane receptor mediated method. It is understood the exemplary process can influence singly or in combination external cell membrane receptor(s) as well as nuclear cell membrane receptor(s), including agonist, antagonist, inverse agonist, calcium ion and sodium and potassium channels, cell-to-cell communication both in vitro or in vivo. Moreover, it is understood that the system/method can influence intracellular charge and functioning of intracellular organelles and structures and processes, such as mitochondrial functioning, protein synthesis, and the process and phases of mitosis. As one example, for in vitro or in vivo situations to influence the process of mitosis and other cellular functioning for purposes of treating plant, animal and human cancers; and/or for in vitro/vivo for extracellular charge and interstitial fluid fields of a plant, animal or human body; or for cellular autophagy and mitochondrial biogenesis.

Accordingly, the intensity modulation capability of one or more of these embodiments is believed to significantly improve electro-therapy treatment responses in conditions such as: Pain, Inflammation, Shingles pain (Varicella zoster), Macular Degeneration, Psychological Mood, skin Cosmetic concerns and wrinkles, nausea, PMS, injury or trauma, wound healing, etc. The ability to improve or potentiate Iontophoresis treatment responses and/or depth of penetration of the involved compounds and/or medications(s) is also believed to be enhanced. Electro-therapy treatment, previously known in the prior art to be unresponsive or inefficacious for Hepatitis, Nephritis, Interstitial Cystitis, high blood pressure, Benign Prostatic Hypertrophy (BPH), Prostatitis, etc., can be effectively treated by various embodiments described herein. Various embodiments are understood by the inventor to positively affect cellular physiologic and/or nuclear (e.g., genetic, etc.) structure and/or functioning in tissues not only in vivo, but also in vitro, as well as improving or potentiating cellular electroporation methods known in the art.

Various embodiments are understood to have the ability to influence biological systems at a cellular level, organ level and organism level, including rate of cellular proliferation growth rates (both enhancing and inhibiting) as well as differentiation into the various specialized cellular sub-types as well as de-differentiation, cellular telomeric attrition, cellular membrane phospholipid dynamics, cellular membrane protein activation and/or deactivation; hormonal, immunologic, peptide, protein and other cellular signaling systems; up regulation and down regulation of various genes of interest, etc.

Details of these and other embodiments with their capabilities and therapeutic techniques are further described below.

FIG. 1 is an illustration 100 of a self-enclosed embodiment on the back of a horse 110. A protective housing 130 contains the (not shown) power supply, a microchip or microprocessor, associated frequency/current controller, active state indicator and one or more channels for applying microamperes of electrical current to the skin of the horse 110. The channels are coupled to embedded electrodes and/or current paths in the pad 120 to contact desired treatment areas. The controller device is not user accessible, being encased in the protective housing 130, and provides a programmatically controlled, systematically changing amount of current in each channel from about 0 microamperes to about 600 microamperes. The frequency function is programmatically controlled, by the microprocessor, and systematically changing from direct current to about 1,000 Hertz or more. The other parameters of electrical output such as duty cycle, waveform, polarity, etc. are also programmatically controlled and systematically changing.

The above embodiment is representative of one of many possible configurations, but exemplifies a commercial embodiment, with the specified current and frequency values, that has been used for treating animals. Of course, other configurations, modifications, applications are possible and, being within the purview of one of ordinary skill in art, are within the scope and spirit of this disclosure.

Figure 2:
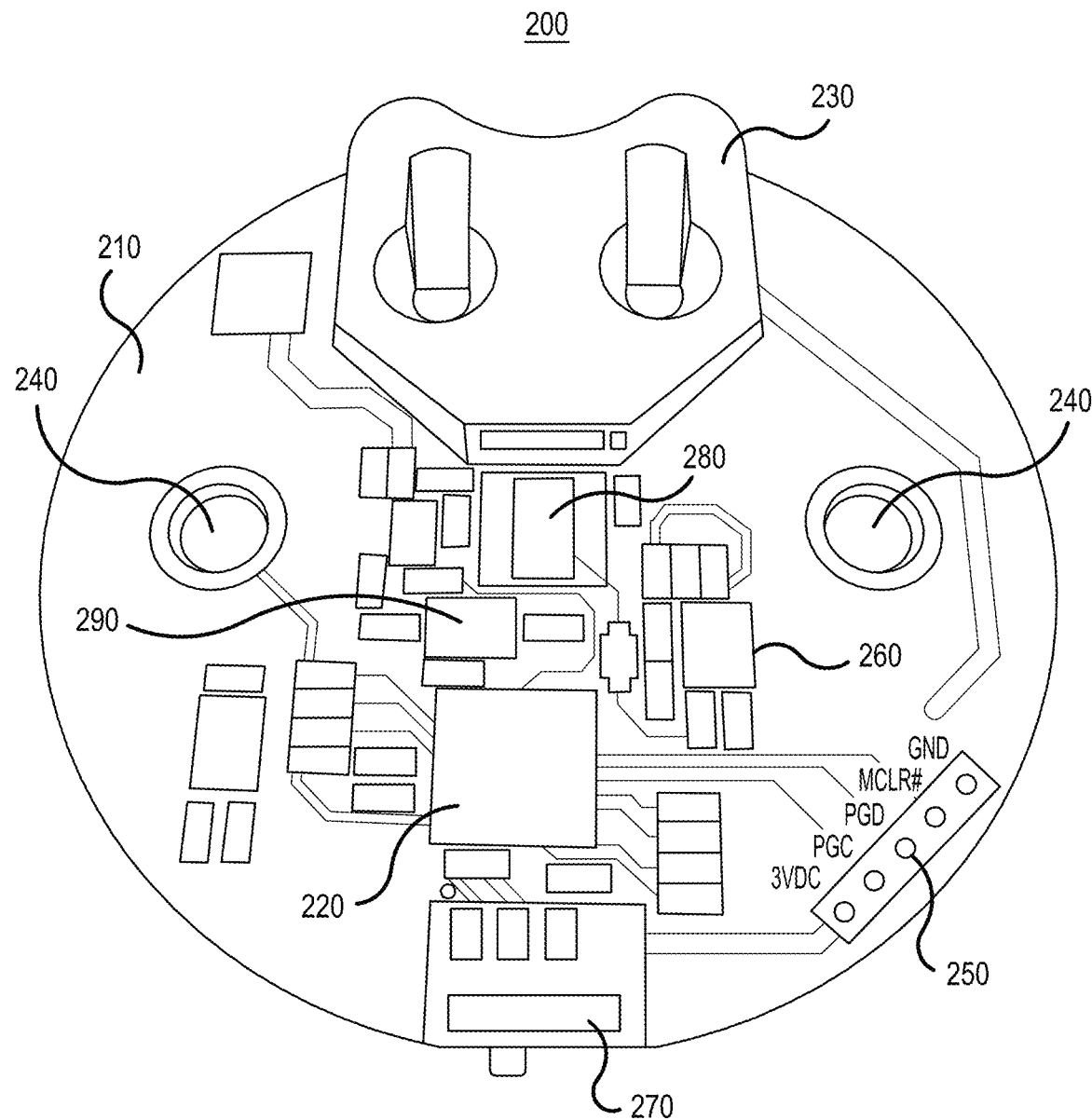
FIG. 2 is an illustration of an exposed controller comprising circuit board.

FIG. 2 is an illustration 200 of an exposed controller comprising circuit board 210, microprocessor 220, battery chamber 230, two channels 240 for electrode contact having outer "snap-in" collars for attachment, and input/output pin 250. DC/DC step up converter 260, on/off switch 270, status light 280, frequency crystal 290, with discrete circuit elements are disposed about circuit board 210. Battery chamber 230 houses the battery (one or more may be used to obtain the desired voltage/current). Microprocessor 220 (or associated memory) contains the program for controlling the output such as duty cycle, waveform, polarity, etc. In some embodiments, channel 240 may be connected to only one electrode, according to design preference. An instance where this could occur would be if the subject had a natural polarity opposite to the single channel 240. Or, a buildup of charge is intended by the therapy.

Figure 3:
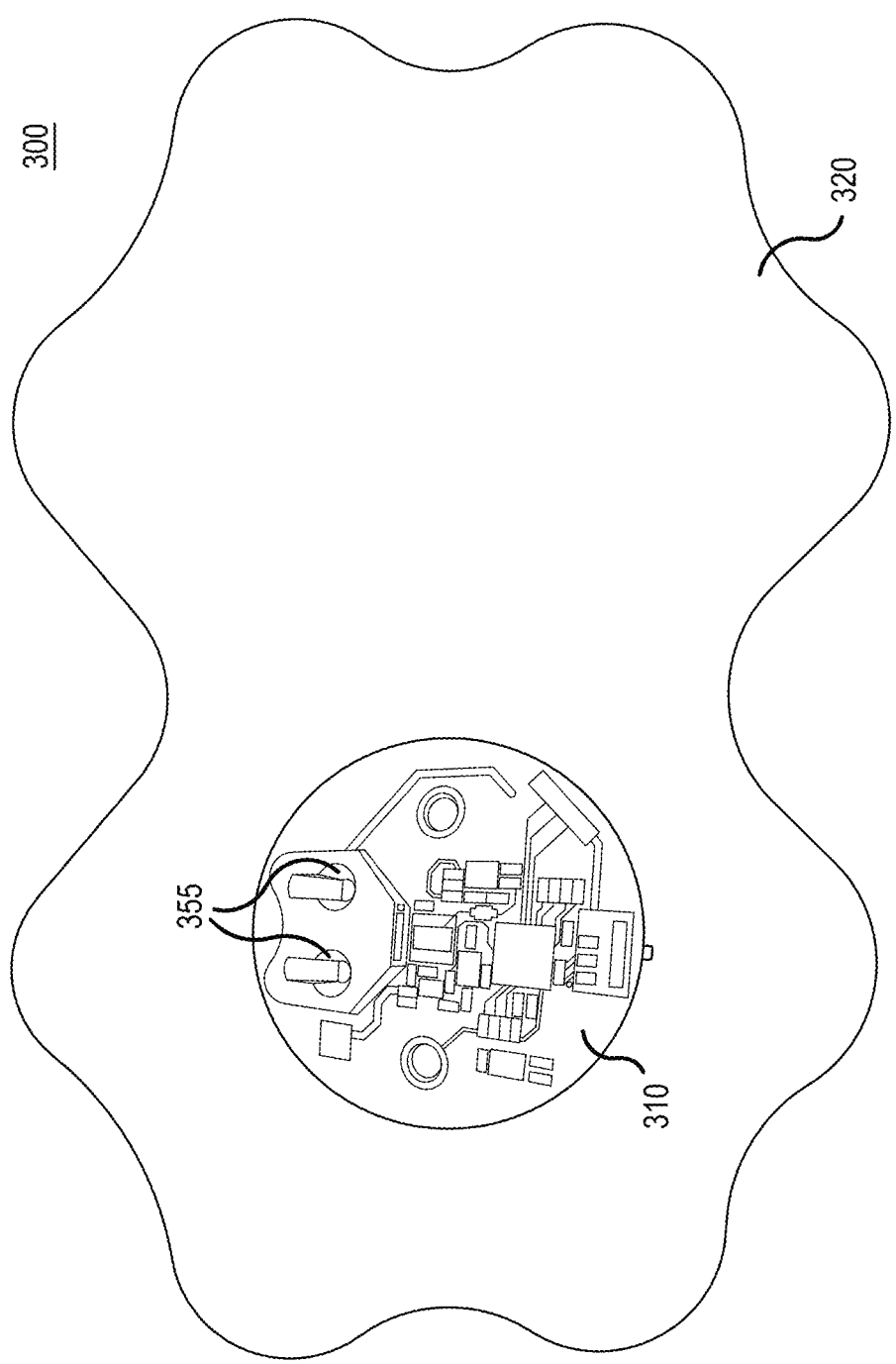
FIG. 3 is an illustration of an exposed controller attached to an electrode pad, with batteries installed.

FIG. 3 is an illustration of an exposed controller 310 attached to an electrode pad 320, with batteries 335 installed. The overall shape of this electrode pad 320 is designed to be symmetric to allow the entire pad to rest in a balanced manner over the horse's back (or other subject feature). Symmetry keeps the electrode pad 320 balanced so as to minimize slipping during slight movements by the horse (human, plant and/or microbial tissue) and also with its extended surface area and adhesive properties of an electroconductive hydrocolloid gel provides sufficient downward force to ensure that the underside electrodes physically contact and adhere to the tissue as well as conduct the current through the hairy coat of an animal.

As to the specific shape and size of the electrode pad 320, it can be sized to provide a range of "current densities" as it disperses the current from the controller's channel(s) to the anode and cathode. In a commercial embodiment, the electrode pad 320 uses a 64 square centimeter dispersion surface area for the anode and another 64 square centimeter dispersion surface for the cathode. A "Shuriken" (hexagonal shape with extended edges) shape creates a dispersion surface that increases the perimeter length of the pad's electrode relative to the central energized area of the pad's electrode, encouraging a dispersion gradient from the central area of the pad's electrode to the perimeter that changes/pulses partly as a function of the distance from the central discharge area and partly as a function of the waveforms changing with the controller's current management program.

The extension "nubs" (or undulating edge) of the electrode pad 320 also serve to improve the ability of the electrode pad 320 to form to curved surfaces of the subject's body, therefore improving treatment effectiveness by improving body surface contact/tissue electrodispersion. These extension "nubs" also improves usability, in contrast to a typical medical device (electrode) that traditionally utilizes square, circular and rectangular designs that are built for ease of manufacture, but not for facilitation of electrotherapy to a body composed of very few flat surfaces.

In a commercial embodiment, the electrode pad 320 is configured to have mating snap connectors to allow the controller 310 to "snap" into the electrode pad 320, to form the electrical connection and also be secured to the electrode pad 320. The makeup of the electrode pads 320, depending on application, can be composed of a material that has been tested for biocompatibility, allergenicity, cytotoxicity, and engineering verification and validation. Depending on implementation, the electrode pad 320 may need to be FDA compliant, or compliant with any other medical device/treatment approving body.

Figure 4:
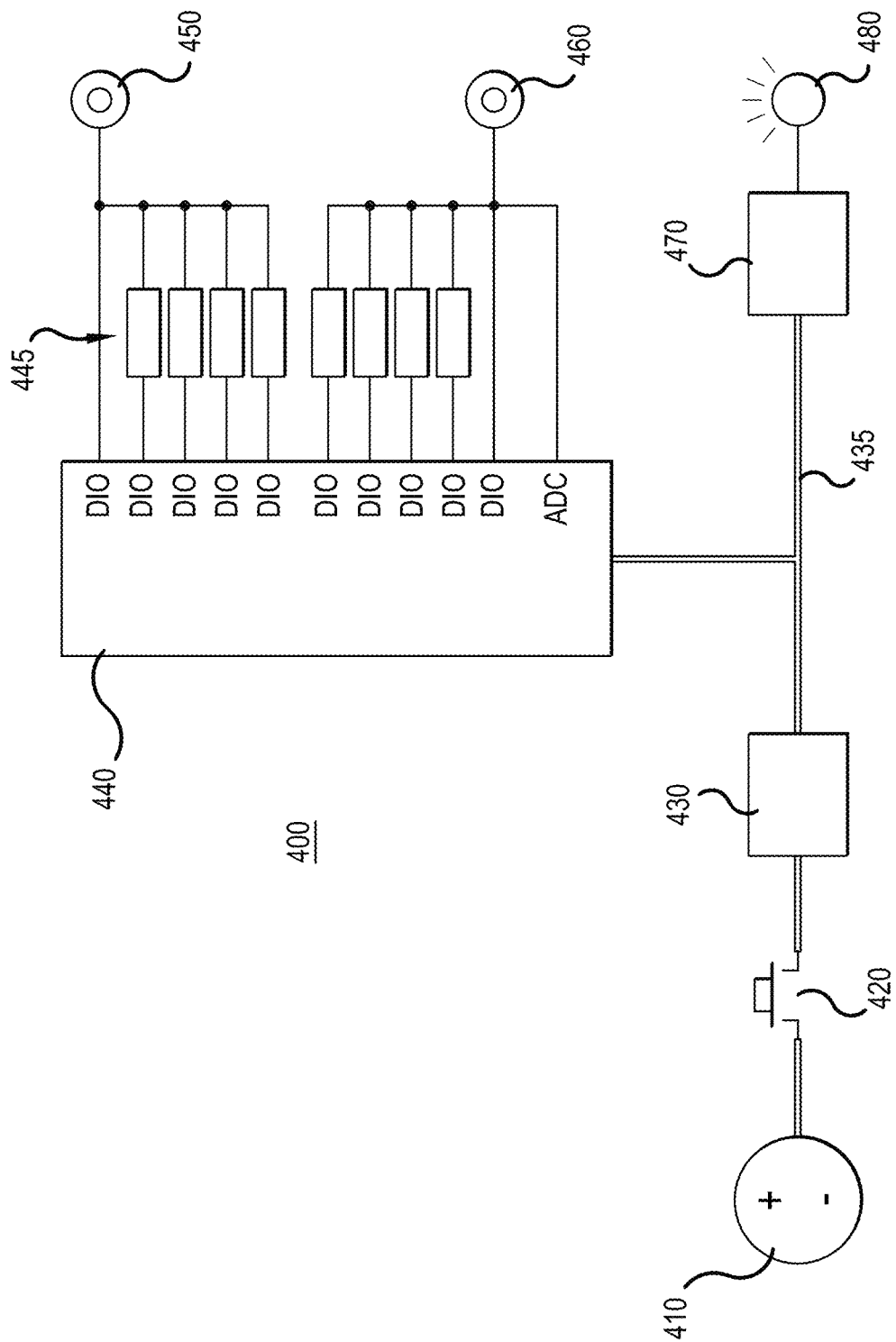
FIG. 4 is a block diagram of a device embodiment.

FIG. 4 is a block diagram 400 of a device embodiment. Power source 410 is coupled to an on/off switch 420 which is connected to a boosting converter 430, which boosts the power source 410's voltage to a higher level (if power source 410 is of sufficient voltage/current, then boosting converter 430 may be bypassed or deleted from the design). The boosted voltage is channeled via power rail 435 to status indicator electronics 470 which feeds status indicator 480. The status indicator 480 will typically be an LED, but may be another light emitting device, and/or be proxied by a sound emitter. Status indicator electronics 470 can generate a blinking/varying signal to status indicator 480, or may be a steady state signal. Of course, other types of signals and/or indicators 480 may be used without departing from the spirit and scope of this disclosure. Moreover, more than one status indicator 480 may be utilized, according to design preference.

Power rail 435 (or by separate connection from power source 410—not shown) carries power to microprocessor 440, which contains the program/instructions for controlling the output such as duty cycle, waveform, polarity, etc. The program may be activated by initiation of the on/off or momentary switch 420 or upon some other trigger. Microprocessor 440 has output channels 450, 460 which are the channel electrodes forwarding the current signals to the subject. Various resistors/switches/controls 445 may be switched on/off via signals from microprocessor 440, to modulate/alter the output current to output channels 450, 460.

This embodiment contemplates the frequency control to be part of the microprocessor 440. That is, frequency control actions are facilitated by software instructions. However, the actual frequency "source" may be a clock signal external to the microprocessor 440 or internal to the microprocessor 440. Understanding that some clock sources can generate multiple frequencies, more than one clock source may not be necessary. Therefore, microprocessor 440 may rely on internal frequency changing/amplitude changing capabilities or rely on other chips (not shown) that may be more effective in providing the desired control. Therefore, multiple chips may be used according to design preference. Aspects of microprocessor and/or chip level control/manipulation of signal frequency and amplitude are well known and, therefore, the details thereof are within the purview of one of ordinary skill in the art.

FIGS. 2-4 are demonstrative of sample hardware devices capable of providing the desired signals. Since there are myriad of ways to provide circuitry to generate the desired signals, it is understood that one of ordinary skill in the art may devise numerous types of alternative configurations, limited only to design preference. Therefore, changes, modifications, variations to the hardware shown in FIGS. 2-4 are understood to be within the purview of one of ordinary skill and within the spirit and scope of this disclosure. As one example, a practitioner may be able to apply therapeutic touch, massage, acupressure, physical therapy, osteopathy, etc. to an animal or human through electroconductive gloves with the device transmitting the method to the gloves and the gloves (optionally) connected to each other either by means of a wire or wireless connection.

As another example, it is contemplated that hardware and software can be developed to have the system operated through a software "App." That is, App-enabled external device (e.g., smart phone or smart device) can communicate with a microchip embedded in or to a permanent or disposable electrode attached to the user's skin or to an implanted device, allowing the user to make various adjustments in output or choose a specific therapy program sequence. The App can also collect user responses regarding treatment efficacy. The breadth of this App can be expanded to include large scale user data collection and analysis, payment, updates, subscription, multi-user subscriptions, etc. As one non-limiting example, a user-controlled device could use user-feedback (via the App) to determine the appropriate signal configuration/intensity/duration for a given treatment. The App could provide the user a list of recommended choices under the treatment regimen and evaluate the user's progress, under a pay-per-use account.

Figure 5:
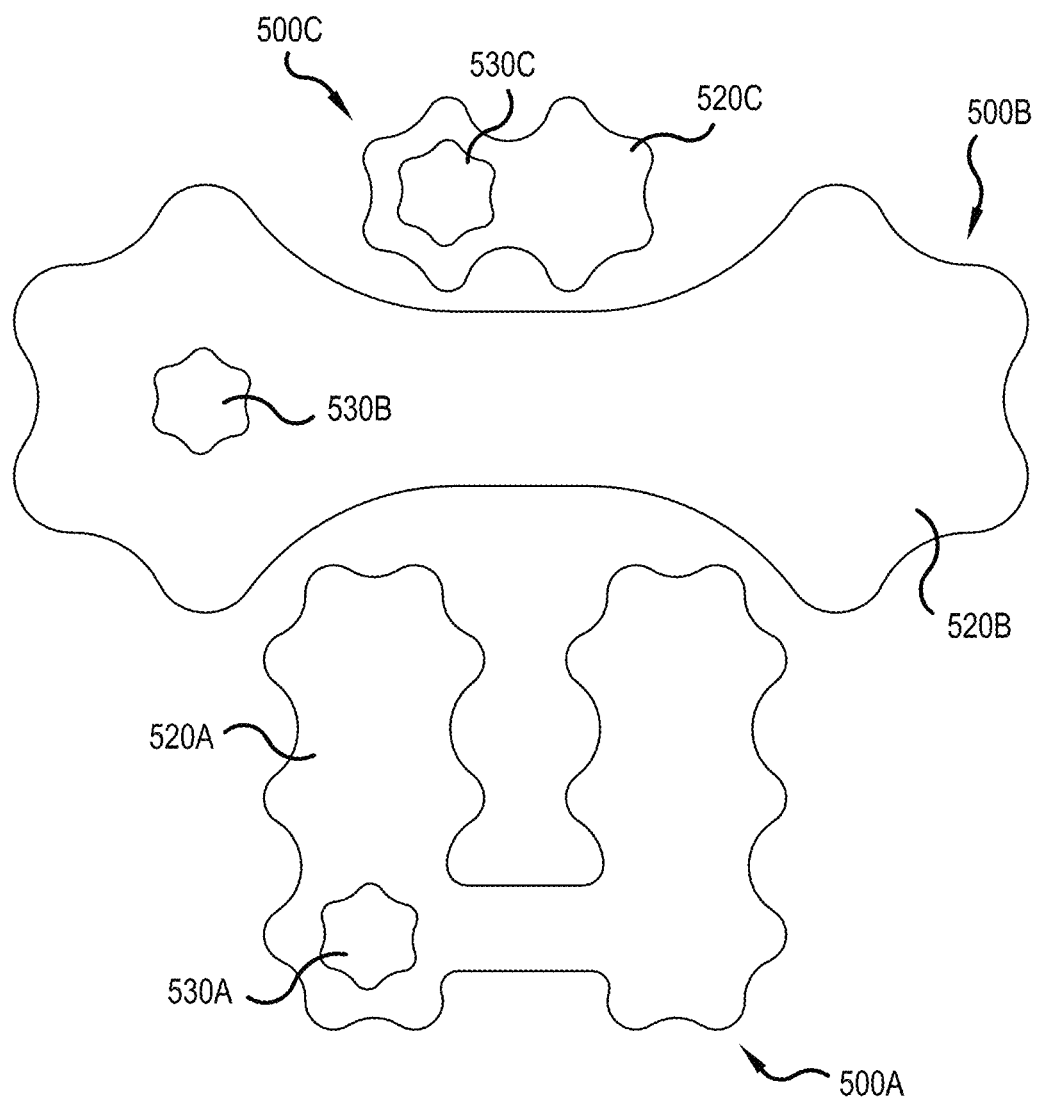
FIG. 5 contains illustrations of various electrode pad configurations with attached controller.

FIG. 5 are illustrations of various electrode pad configurations with attached controller. The lower illustration shows an embodiment 500A with electrode pad 520A and controller 530A attached thereto. Pad 520A is shaped as a horseshoe so as to rest over or fold over a neck, back, or shoulder, etc. The middle illustration shows an embodiment 500B with electrode pad 520B and controller 530B attached thereto. Electrode pad 500B is shaped as a long "double shuriken" to cover larger areas for treatment (e.g., horse's hind quarters). The upper illustration shows an embodiment 500C with electrode pad 520C and controller 530C attached thereto. Electrode pad 500C is shaped as a small double shuriken for smaller treatment areas. It is noted that these embodiments show symmetrically shaped electrode pads 520A, 520B, 530B. Of course, it may be desirable in some embodiments to have non-symmetric electrode pads or of differently shaped electrode pads. Therefore, these considerations of shape and symmetry are dependent on the application and accordingly may be modified, altered without departing from the spirit and scope of this disclosure.

For a non-limiting example, an electrode pad can have several sections, e.g., a two piece electrode pad with the controller device snapping onto one side and each electrode pad piece shaped with the "Shuriken" design with an electroconductive wire between the two electrode pad pieces.

Some variations of these embodiments can be:

A disposable system, where the controller is attached to the electrode pad which has a limited service life and the electrode pad alone is thrown away after its service life has expired; or a part of or the entirety of the pad is disposable—single use or limited multiple use;

The controller is "integrated" into the electrode pad, being built and fabricated as a non-detachable single piece unit. Such a system could also have a limited service life, wherein the entire system is disposed of; and The controller could have a wireless chip, communicating information, status, etc. wirelessly to a remote device, such as, for example, a smart phone. This would be beneficial for situations where the user could choose different treatment options (e.g., low back, knee, elbow, etc.), query to determine the "stage" of treatment, percent of current flow being transferred through the tissue to the reference electrode, health of controller battery, etc.

Therefore, it should be apparent that various modifications and changes may be made without departing from the spirit and scope of this disclosure.

Figure 6A:
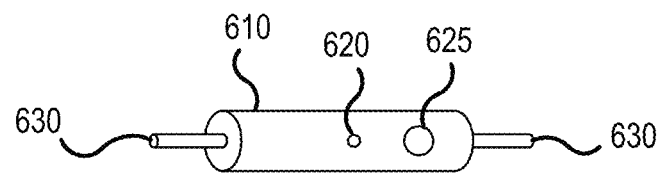
FIGS. 6A, 6B and 6C are illustrations of alternate self-contained controller shapes with external electrode connectors
Figure 6B:
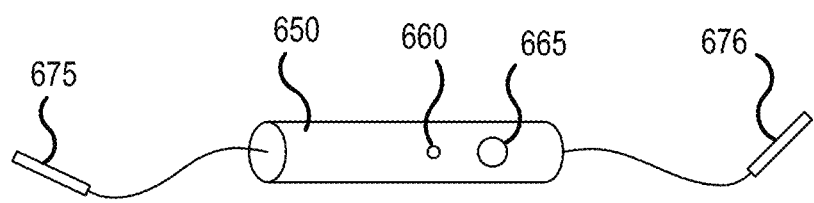
Figure 6C:
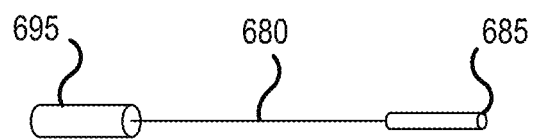

FIGS. 6A, 6B and 6C are illustrations of alternate self-contained controller shapes with external electrode connectors. FIG. 6A is an illustration of a "cylindrical" controller housing 610 with indicator "light" 620 and reset/power button 625 on its surface. Ends of the housing 610 contain external electrode connectors 630 which can be plugged into to whatever connector arrangement is found on the pad (not shown) or contacting element. In one embodiment, the external electrode connectors 630 can be rigid male pins, to mate female connectors on/in the pad/contacting element. Of course, other types of connectors may be devised, according to design preference.

FIG. 6B is an illustration of another "cylindrical" controller housing 650, with indicator "light" 660 and reset/power button 665 on its surface. Ends of the housing 650 contain flexible lines terminated with electrode connectors 675 which can be connected to whatever connector arrangement found on the pad (not shown) or contacting element.

FIG. 6C is an illustration of an electrode connector extension 680, having a male style connector 685 on one side and a female style connector 685 on the other side. This extension embodiment contemplates having the controller connected in a non-rigid fashion to a pad (not shown) or contacting element.

It should be appreciated that while the above embodiments are described in the context of an enclosed controller administering electro-therapy via contact through a pad (or electrode extension) to the subject, via electrical waveforms shaped as further detailed below, the actual shape/design of the controller and/or pad and/or extension may be altered, modified according to design preference. So, if design preference is to apply the above embodiments, for example, to a laboratory situation or medical environment, the above designs may be easily modified to provide the desired effect. For example, if the subject is laboratory-housed tissue or culture of cells, etc., the contacts of the controller can be redesigned to allow the appropriate signals to be fed to the tissue or culture of cells, to the appropriate subject contacts. Accordingly, in these and other instances, different designs/implementations of the controller and its contacts/electrodes, etc., with consideration of the nature/type of electrical signals being generated to achieve the respective effect on the subject material, may be contemplated without departing from the spirit and scope of this disclosure.

As one non-limiting example, the electrodes could be formed of a long conductive strip that is placed within or on a flexible sleeve, the sleeve being worn on the limb of a person or animal. The sleeve could also be open, being simply a wrap or even a strip of adhesive material that is adhered to the skin or body of the user, wherein the electrode(s) may span the length of the wrap/strip. A plurality of electrodes could be distributed throughout the sleeve, wrap, or strip for different "zones" of current, or different "densities" of current. In other examples, only a single "long" electrode may be utilized. The utility of such a "wrap" or "strip" embodiment in the sports field is understood to be very desirable.

Figure 7:
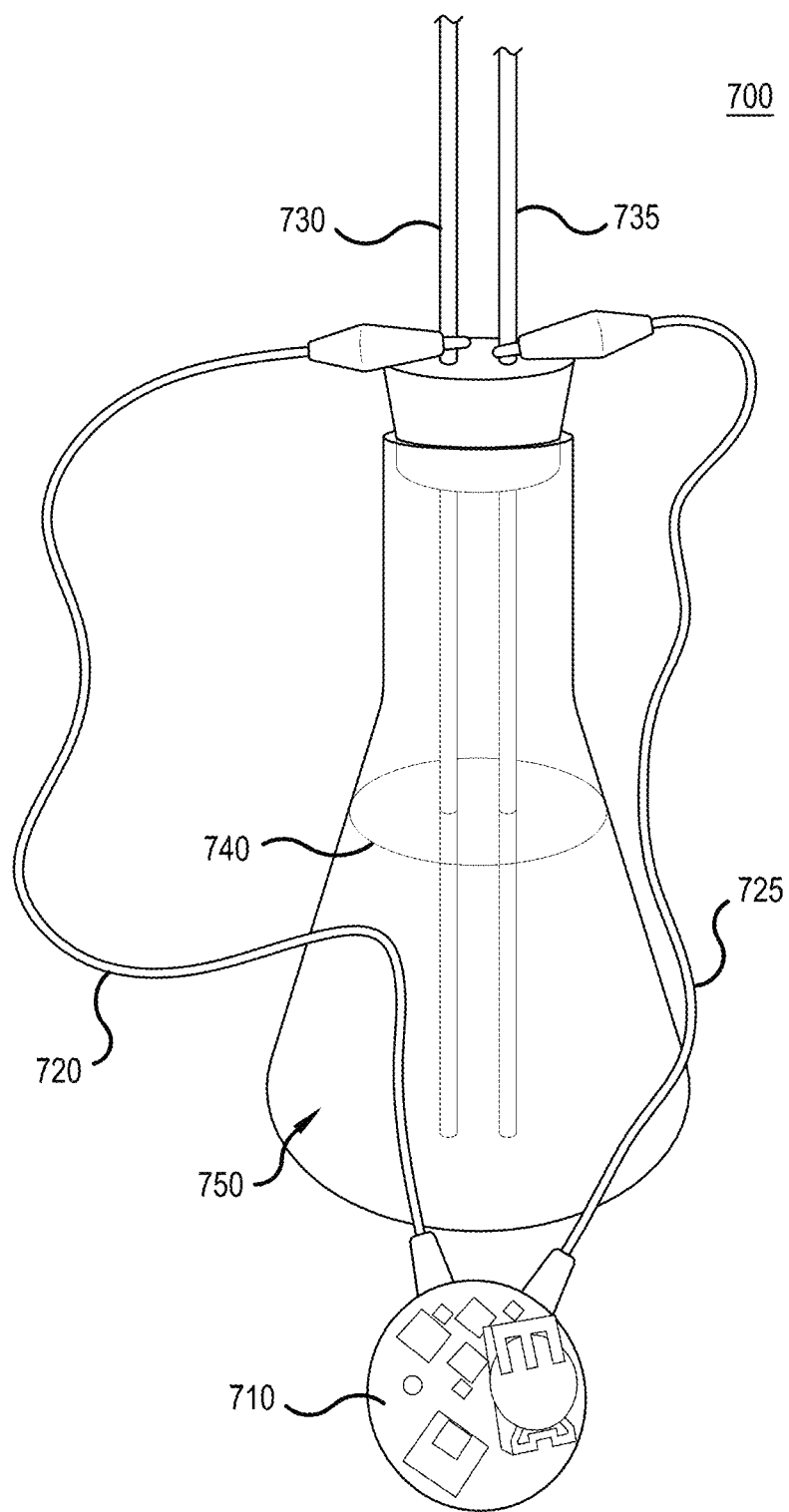
FIG. 7 is an illustration of an embodiment applied to a flask of cultures.

FIG. 7 is an illustration 700 of an embodiment rudimentally applied to a flask of cultures. Exposed controller device 710 has its electrode channels connected by simple alligator clips 720, 725 to rod electrodes 730, 735. The rod electrodes 730, 735 are submerged into culture solution 740 that is housed by flask 750. This embodiment illustrates the application of an embodiment without a corresponding electrode pad and is demonstrative of the multiple "subject" applications possible.

Figure 8:
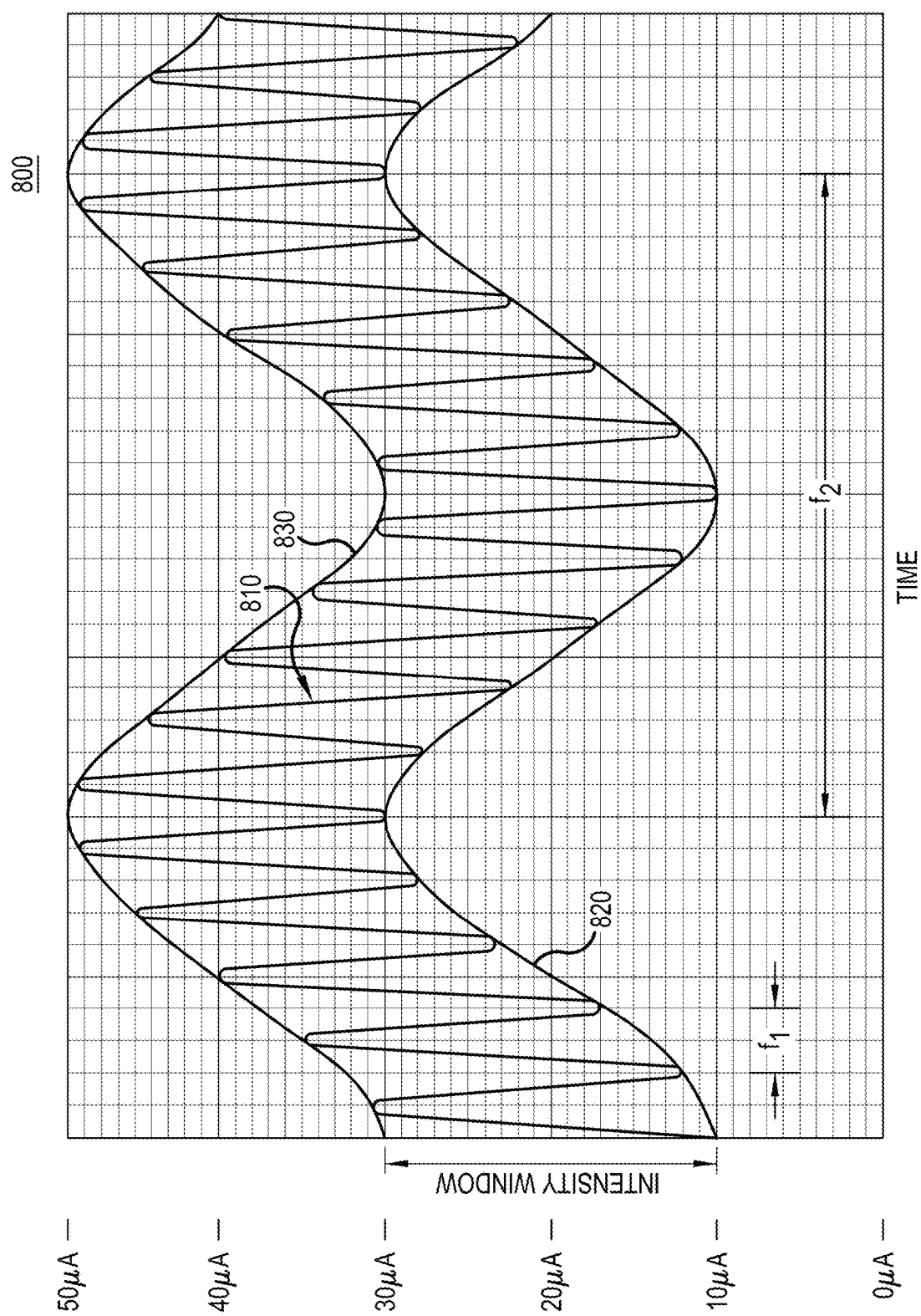
FIG. 8 is a plot of one embodiment of a representative signal waveform.

FIG. 8 is a plot 800 of one embodiment of a representative signal waveform. The time-harmonic or frequency based waveform is composed of high frequency $f_1$ signal 810 being amplitude modulated according to a lower frequency $f_2$ signal to form a fixed separation (or current intensity window—CIW) having a minimum 820 and maximum 830 envelope. It is evident that this signal waveform is wavelike in form and has a positive DC offset of approximately 20 uA, with a cyclical amplitude modulation range of 20 uA. The combination of the two frequencies ($f_1$, $f_2$) and offset generates a current signal that has a 50 uA peak and a 10 uA floor, but fluctuates between the peak and floor values. In this example, the lower frequency (carrier) $f_2$ is one-tenth the frequency of the higher frequency $f_1$ signal. A corresponding set of frequencies would be 3 Hz and 30 Hz, or 10 Hz and 100 Hz, and so forth. Of course, other frequency ratios may be used, according to design preference, as well as DC offsets.

The intertwining of the high frequency $f_1$ signal 810 within the CIW envelope creates a current "density" within the CIW, that more slowly fluctuates in overall amplitude with the lower frequency modulating signal 830. This provides a unique electro-therapy signal profile, one that fluctuates very rapidly within a small time frame (aka—high frequency signal $f_1$), while in the aggregate (CIW) fluctuates very slowly (aka—low frequency signal $f_2$). Further, with the DC offset, a total of three effects are being applied simultaneously.

The embodiment of FIG. 8 shows one configuration where the core amplitudes of the low and high frequency signals are fixed ($f_1$ relative displacement is 20 uA, and $f_2$ relative displacement is 20 uA, where the composite signal is different). If either $f_1$ or $f_2$ are not amplitude fixed (held constant), then the composite signal will have a different profile (the CIW envelope will change), but still provide multiple frequency dependent signal effects that are beneficial.

Figure 9:
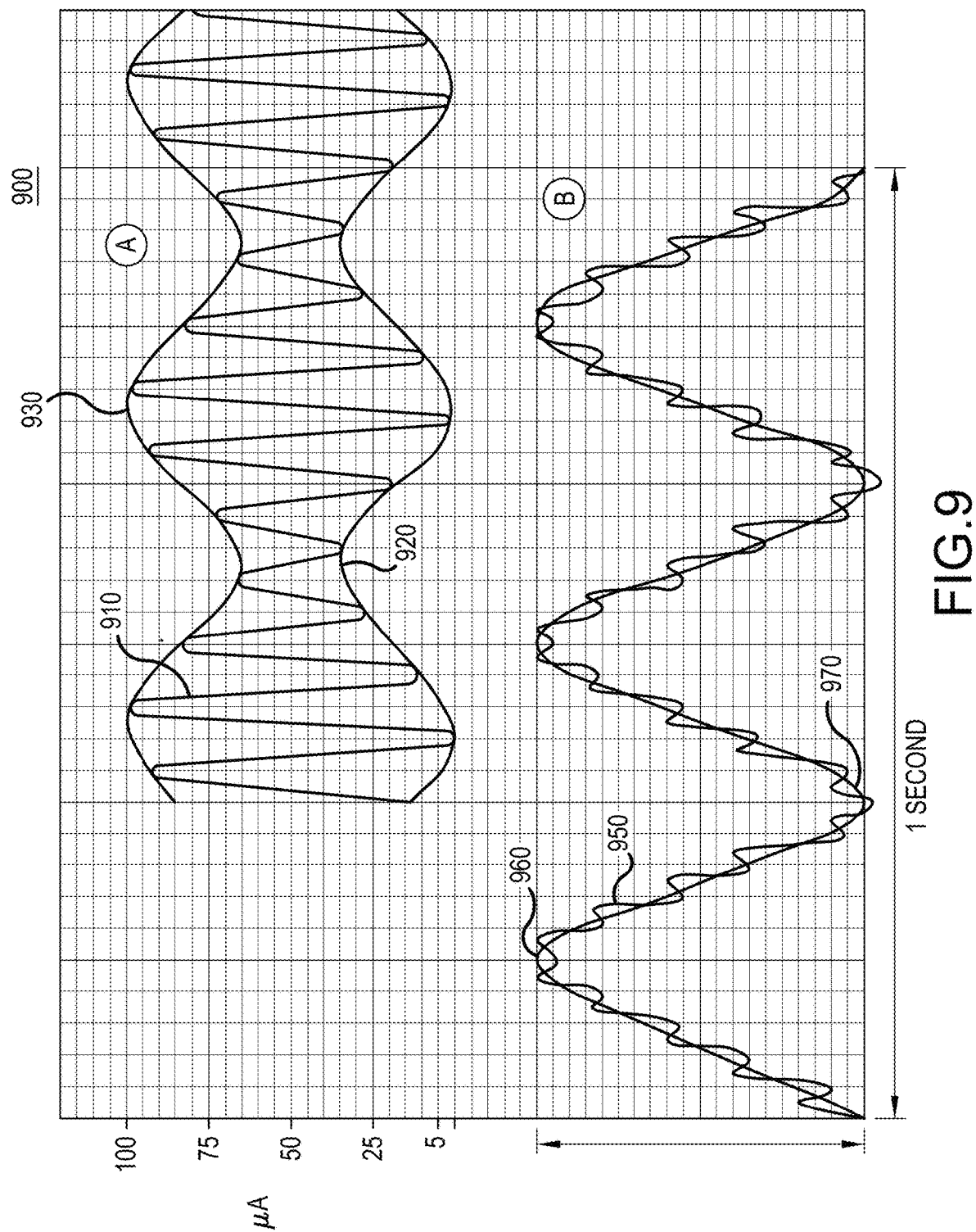
FIG. 9 contains graphical representations of various modulated signals, bounded by varying microamperage values.

FIG. 9 contains graphical representations of various amplitude modulated signals, bounded by two varying microamperage values. Referring to example A, higher frequency signal 910 is amplitude modulated with a lower frequency signal 920, to form a CIW envelope that is symmetric across the 50 uA midline (a DC offset of 50 uA is implicit). This example contemplates a larger high frequency "swing" from peak-to-trough, the higher frequency swing becoming smaller for a period and then larger and then repeating, as a function of the lower frequency signal 920, as seen in the humps of example A. This particular embodiment shows a max current applied as 100 uA, and a min current applied as 0 uA, with a CIW that varies in aggregate current "density" in accordance to the lower frequency signal 920 component. This can be further extrapolated to form a "pulsing" wave or other variations.

Referring to example B, higher frequency signal 950 is amplitude controlled by the lower frequency signal having its peak 960 and trough 970. Here, the amplitude of the lower frequency signal is held constant while the higher frequency signal 950 is "rippled" over the lower frequency signal. In this example, the higher frequency signal is at 30 Hz, while the lower frequency signal is at 2 Hz. Evident in this example is the fact that the CIW (excursion of one cycle of higher frequency signal 950) envelope is very small in comparison to the overall low frequency range (excursion of one cycle of lower frequency signal). It should be understood that while FIG. 9 shows specific current values and specific time period for the respective frequencies, these values are representative of one possible embodiment and other values may be used, depending on the implementation preference.

Figure 10A:
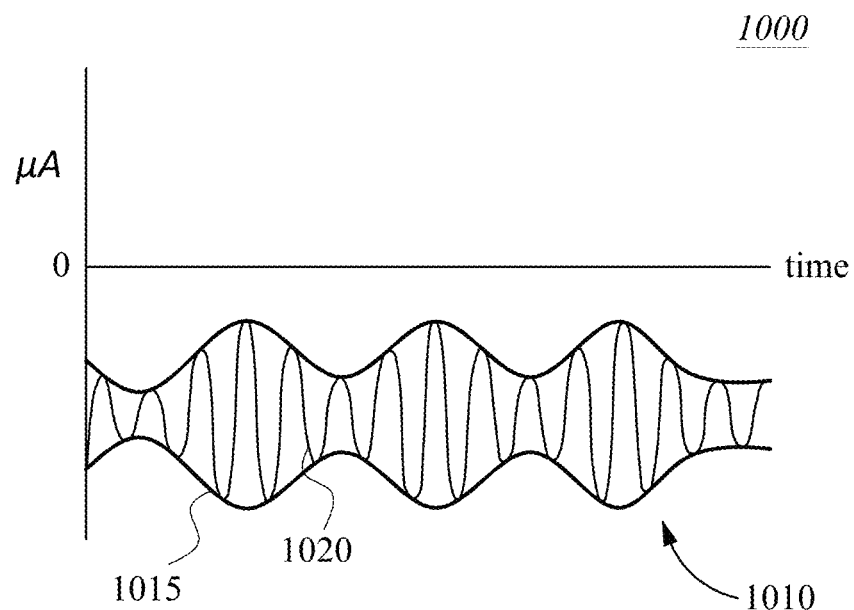
FIGS. 10A-B are plots of alternative embodiments of representative signal waveforms.

FIG. 10A is a plot 1000 of an alternative embodiment of representative signal(s) waveform 1010. Here, FIG. 10A shows overall signal 1010 with a "uniform" negative DC offset to produce a lower frequency modulating signal 1015 forming a symmetric CIW envelope bounding higher frequency signal 1020. As is apparent, the overall signal 1010 value is negative. Of course, both here and in the other embodiments shown, the entirety of signal 1010 may not be negative, but some portion of it may become positive, if so desired. This may also be achieved by varying the DC offset value, raising, lowering the signal 1010 as a function of time.

Figure 10B:
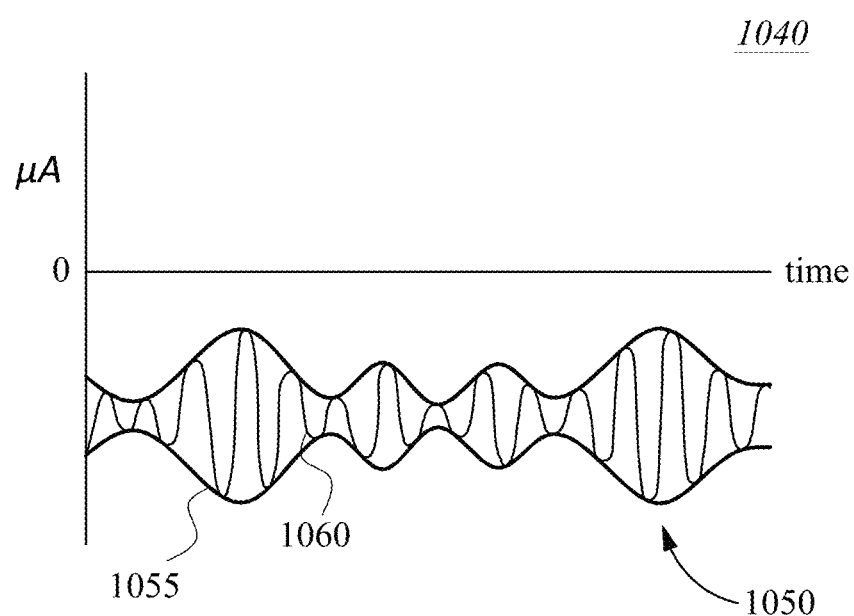

FIG. 10B is a plot 1040 of an alternative embodiment of representative signal(s) waveform 1050, where the lower frequency modulating signal 1055 forms a non-uniform CIW envelope bounding higher frequency signal 1060, and with a negative DC offset. This illustrates the ability to vary the peak amplitude of signal 1055, if so desired.

Figure 11A:
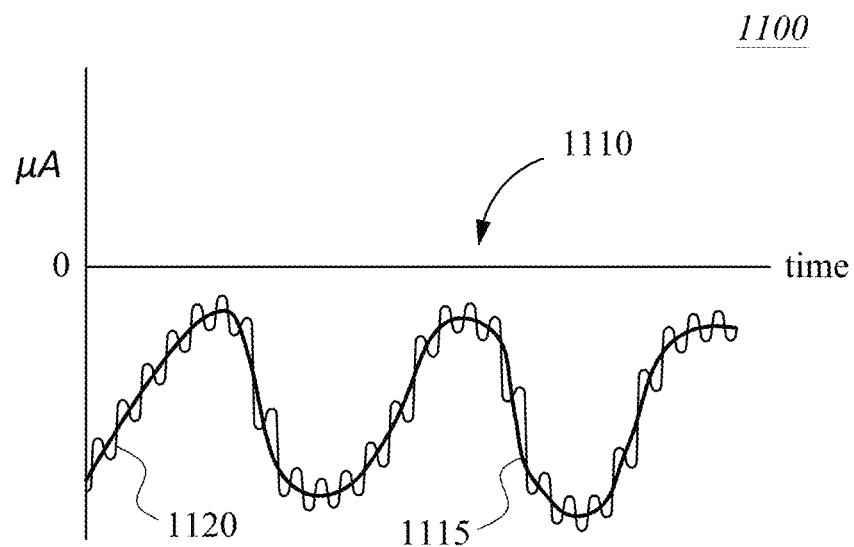
FIGS. 11A-B are plots of alternative embodiments of representative signal waveforms.

FIG. 11A is a plot 1100 of an alternative embodiment of representative signal(s) waveform 1110, where the lower frequency modulating signal 1115 with higher frequency signal 1120 is negative.

Figure 11B:
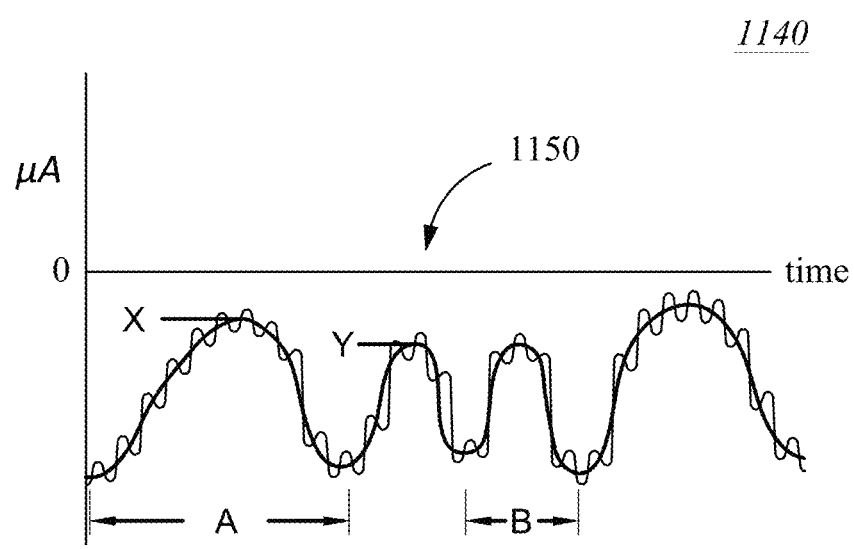

FIG. 11B is a plot 1140 of an alternative embodiment of representative signal(s) waveform 1150, where the modulating lower frequency signal's peak values are varied as a function of time, as evident by the different X and Y heights.

Figure 12A:
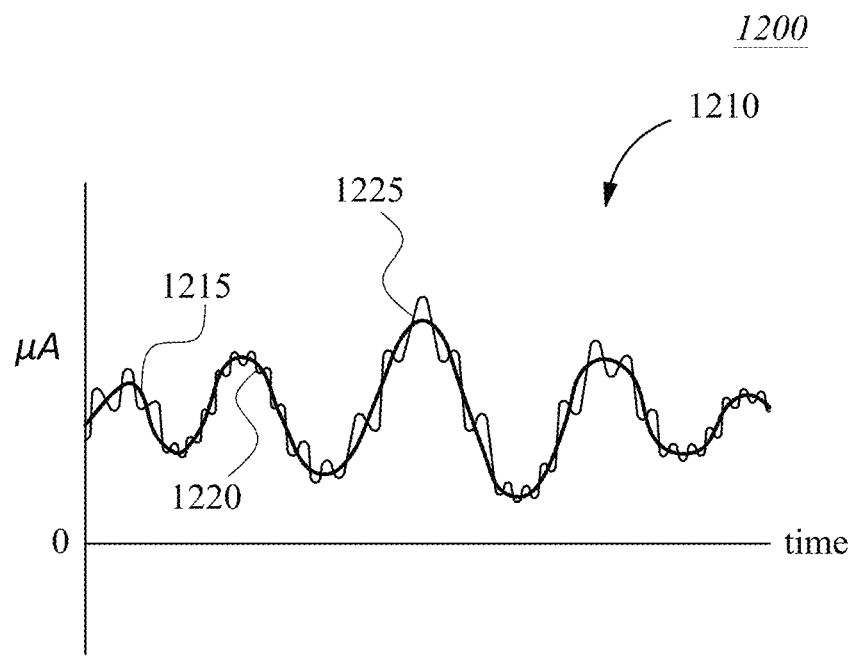
FIGS. 12A-B are plots of alternative embodiments of representative signal waveforms.

FIG. 12A is a plot 1200 of an alternative embodiment of representative signal(s) waveform 1210, where the modulating lower frequency signal 1215 peak amplitude is varied and the frequency of the higher frequency signal frequency is varied, as evident in the different oscillation rates seen at 1220 and 1225 (having the higher frequency than 1220). This embodiment illustrates varying the peak amplitude of the modulating frequency and varying the frequency of the secondary higher frequency.

Figure 12B:
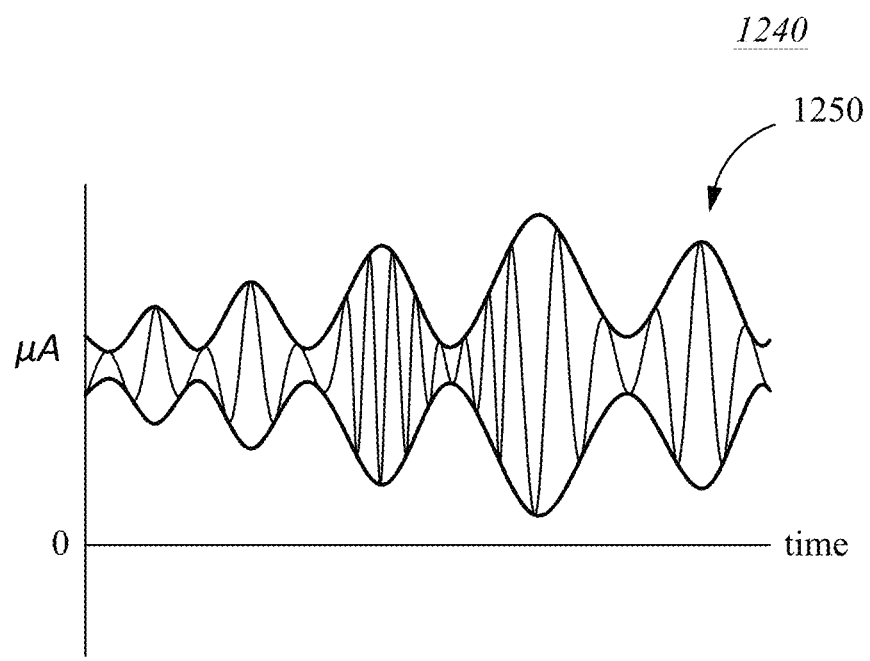

FIG. 12B is a plot 1240 of an alternative embodiment of representative signal(s) waveform 1250, where the modulating lower frequency peak amplitude is varied as a function of time, and the frequency of the higher frequency signal is varied, to form CIW window with different peak values and different energy density.

Figure 13A:
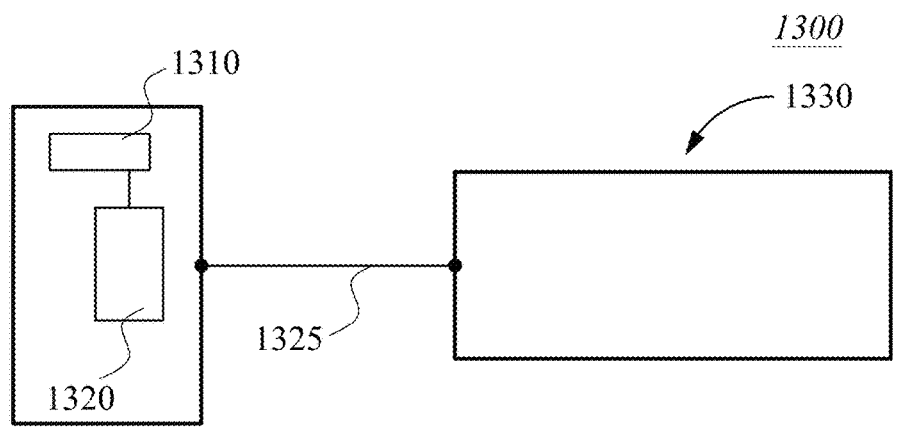
FIG. 13A is an illustration of a testing embodiment.

FIG. 13A is a block diagram illustration 1300 of a testing station embodiment. Block 1330 represents a test chamber with one or more cell cultures/samples therein. Processor/signal generator 1310 controls the amplitude, frequency, duration, etc. of the underlying signals which are forwarded to the testing station 1330 via channel(s) 1325. Optional switch/multiplexer 1320 provides the ability to "switch" different electrode channels on and off, if so desired.

Figure 13B:
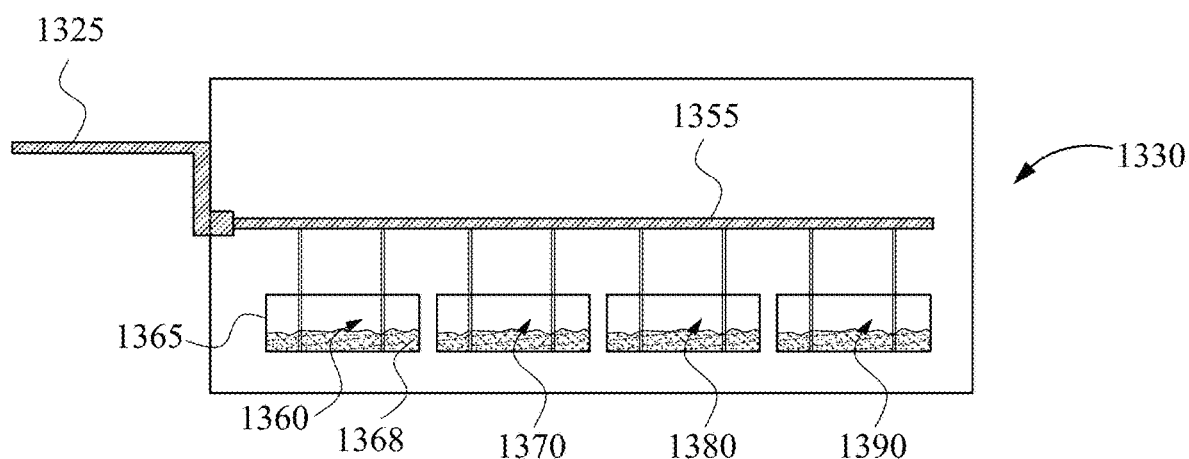
FIG. 13B is an illustration of an embodiment applied to testing multiple cell cultures/samples.

FIG. 13B is an illustration 1350 of a sample automated test system. Signal channel(s) 1325 are dispensed via chamber channel 1355 within chamber 1330. Each container 1365 contains respective culture, tissue, cell, etc. 1368, with container electrodes 1360, 1370, 1380, 1390 disposed within each container and contacting directly or indirectly the sample material. Depending on preference, multiple samples can be treated with the exemplary signals to determine efficacy. The samples may be of different dilutions, types, material, etc. wherein a single or defined "set" of signals are applied to the varied samples, or conversely the samples may be identical with different signals sent to each sample via the respective electrodes to determine efficacy of the signal type used. Of course, combinations of these two approaches and variations thereof may be utilized according to implementation preference. FIG. 13A is presented to illustrate the ability to have a "system" designed for multiple treatments within a test or lab environment.

For example, for research purposes, the effects of electrostimulation on any type of microbiological, plant or animal cell in multi-well cell culture plates can be achieved. The container(s) 1365 can be a culture plate, manufactured with electroconductive materials typical of those used in the PCB industry to provide stimulation to each culture well. The interconnects between chamber channel 1355 and electrodes 1360, 1370, 1380, 1390 can be designed so that each well can be individually and discretely stimulated. The cell culture plate can be docked to a connector (not shown) that allows for wired or wireless connection to an external device, computer and App that is designed to be able to call out and control the stimulation to each well individually in the cell culture plate.

It should be appreciated that the concept detailed in the above FIG. can be reduced to a single container, for example a liquid/dry/materials storage container as used, for example, in the beer, wine, kombucha, yogurt, etc. industries. Therefore, the exemplary system can introduce the desired mixed signal into the container's medium, affecting the storage/shelf life of the organisms therein. It may also be operated to increase the "fermentation" speed of the process, being beneficial to organism growth. Conversely, if it is determined the mixed signal negatively affects the organism's longevity or ability to grow, the system may be used to retard the growth of organisms in the storage container. Therefore, in some embodiments, the mixed signal can operate as a disrupter of biological activity and be used for "sterilization" or prevention of growth (either of the constituent organism or of external, non-desirable organisms).

Figure 14:
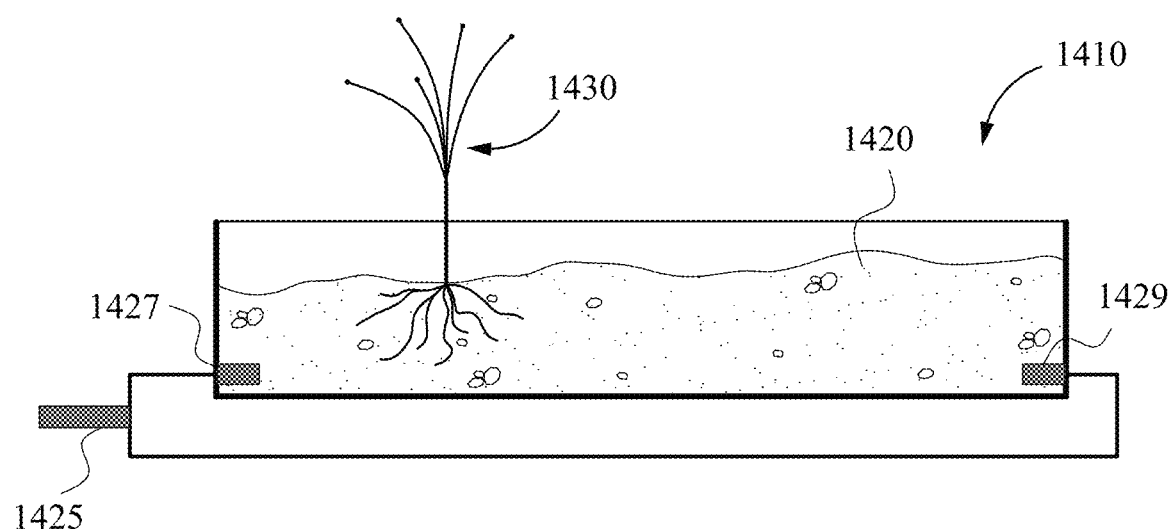
FIG. 14 is an illustration of an embodiment applied to an environment containing living organisms.

FIG. 14 is an illustration 1400 of an embodiment applied to an environment supporting living organisms. Growth chamber 1410 can contain a "bed" of material 1420 for supporting plant or other organism 1430. Material 1420 can be soil, liquid, gel or any constituent material for supporting growth of organism 1430. Electrodes 1427, 1429 can be disposed in the material 1420, being connected to external channel 1425. Of course, while FIG. 14 shows "one" chamber, multiple chambers may be devised.

If the organism 1430 is a plant, electrodes 1427, 1429 can be placed either in, on, or inside the plant to treat plants, especially of commercial significance, for example, viticulture, in order to influence a disease process, infection, decrease water consumption, influence the soil microbiology and fertility, improve or block nutrient uptake, or induce higher yields.

Figure 15:
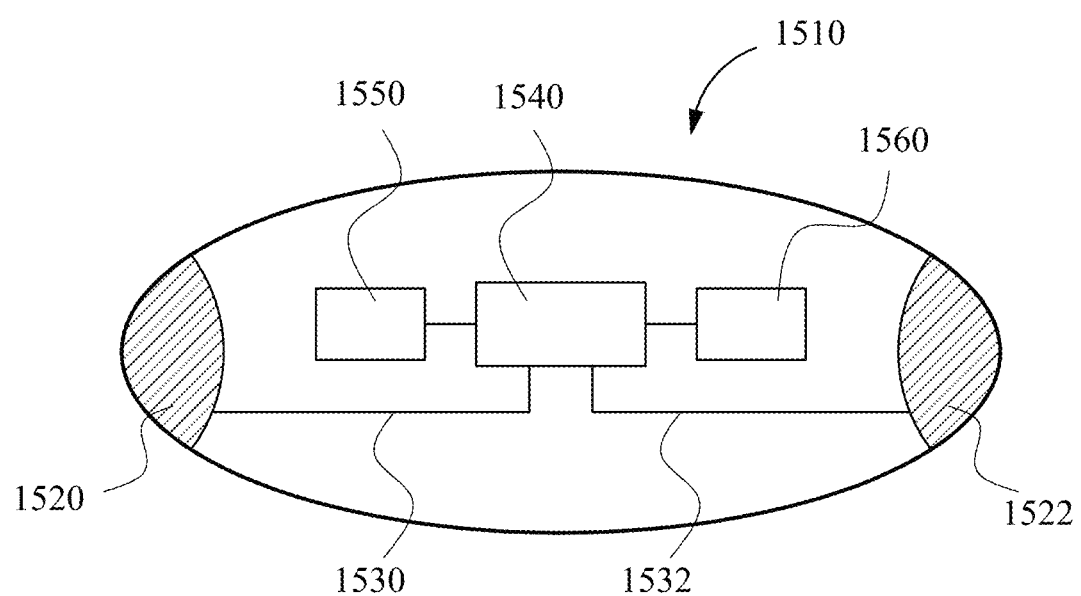
FIG. 15 is an illustration of a "pill" embodiment.

FIG. 15 is an illustration 1500 of a "pill" embodiment. This embodiment is conceived for ingestion by a patient. Pill 1510 can contain electrodes 1520, 1522 that are connected to electrode leads 1530, 1532, respectively, which are connected to controller 1540 generating the exemplary signals. Controller 1540 is connected to power source 1550, providing the necessary power for the signals. Optional wireless/memory module 1560 can provide communication (e.g., location, etc.) to an external device (not shown) or operate as memory source for dictating the signal formats, values for controller 1540.

The ingested pill can produce electrostimulation throughout the area of the intestine that is being targeted as the pill makes its way through the intestinal tract. An alternative approach is the pill may only have a single electrical pole that wirelessly connects to an electrode that is affixed on the abdomen or other area of the body, such as over the spleen or the Vagus nerve. This application of this approach is contemplated for purposes of treating gastrointestinal conditions such as irritable bowel syndrome, colitis, ulcerative colitis, gastroesophageal reflux disorder, diverticulitis, Crohn's disease, celiac disease, gallstone pain, gastroparesis, dysbiosis, food poisoning, intestinal motility disorders such as diarrhea, constipation, etc.

These above embodiments demonstrate a electrotherapeutic technique of systematically modulating the device's output parameters by superimposing multiple waves upon each other allows the application of low microamperage current intensity for longer treatment durations on humans and animals with decreased time to effectiveness, improved treatment efficacy and expanded treatment capabilities over prior art devices. Other embodiments are anticipated and this disclosure only serves as an introduction to the fundamentals of the concept.

Modifications and variations to the above current/signal profiles are contemplated in the context of therapeutic or biological treatments. One example of a variation is by changing the intensity of the output current in a predetermined sequence (increasing and decreasing the microamperage intensity "quickly or gradually" over time between a maximum and minimum value in a stepwise fashion) while keeping the AC frequency and/or DC current and other output parameters that are superimposed on the changing current intensity constant over a period of output time. One non-limiting example would be, 15 uA at 40 Hz for 2 seconds followed by 20 uA at 40 Hz for 2 seconds followed by 25 uA at 40 Hz for 2 seconds followed by 30 uA at 40 Hz for 2 seconds, followed by 25 uA at 40 Hz for 2 seconds followed by 20 uA at 40 Hz for 2 seconds followed by 15 uA at 40 Hz for 2 seconds, etc. Of course, the time periods, frequency, and amplitude may be of different values, according to design preference.

Another example of a variation is by changing the intensity of the output current in a predetermined sequence (increasing and decreasing the intensity "randomly" over time) while keeping the AC frequency and/or DC current and other output parameters that are superimposed on the changing current intensity constant while changing the duty cycle (amount of ON time vs. OFF time within a waveform) of the output in a predetermined systematic way.

Another example of a variation is by changing the intensity of the output current in a predetermined sequence (increasing and decreasing the Intensity randomly over time) while keeping the AC frequency and/or DC current superimposed on the changing current intensity constant while changing the duty cycle (amount of ON time vs. OFF time within a waveform) of the frequency output in a pulsed manner that can be measured in pulses per second or Hertz.

Another example of a variation is by changing the intensity of the output current in a predetermined sequence (increasing and decreasing the microamperage current intensity randomly over time and randomly as a discrete output packet of time duration) while keeping the AC frequency and/or DC current constant and superimposed on the changing current intensity while changing the duty cycle (amount of ON time vs. OFF time within a waveform) of the output in a random pulsed manner that can be measured in pulses per second or Hertz.

Another example of a variation is by changing the intensity of the output current in a predetermined sequence (increasing and decreasing the microamperage current intensity quickly or gradually over time, e.g. systematically as in a step-wise increase and/or decrease of the microamperage level of current intensity output) while changing the AC frequency and/or DC current specifically, systematically and/or randomly and superimposed on the changing current intensity level.

Another example of a variation is by changing the intensity of the output current in a predetermined sequence [increasing and decreasing the intensity in a waveform manner, (e.g. sine wave, square wave, triangle wave, etc.) and quickly or gradually over time and quantified in Hertz or cycles per second, (e.g., a 3 Hz sine wave for 1 minute moving between a lower and a higher microamperage "window of intensity" that said window can vary systematically and/or randomly and sequentially, etc.)] while keeping the AC frequency and/or DC current specific and/or systematically and/or randomly changing and superimposed on the modulating current intensity "waveform."

Another example of a variation is by changing the intensity of the output current in a predetermined sequence [increasing and decreasing the intensity in a waveform manner, (e.g. sine wave, square wave, triangle wave, etc.) and quickly or gradually over time and quantified in Hertz or cycles per second, (e.g., 3 Hz sine wave 1 minute, 40 Hz square wave 3 minutes, etc.)] while changing the AC frequency (including or excluding DC current) systematically (for example with a predetermined sequence, an algorithm, a randomizer and a look-up table, a random value generator, etc.) and superimposed on the modulating current intensity "waveform."

Another example of a variation is by changing the intensity of the output current in a predetermined sequence [increasing and decreasing the intensity in a waveform manner, (e.g. sine wave, square wave, triangle wave, etc.) and quickly or gradually over time between a higher and lower level of microamperes (which acme and nadir can vary at different times) and quantified in Hertz or cycles per second] while changing the AC frequency (including or excluding DC current) in a specified manner (e.g., according to a look-up table) and/or randomly and/or according to an algorithm. For example, a current intensity modulated as a 3 Hz sine wave between a CIW of 10 and 30 microamperes with an AC frequency of 970 Hz square wave superimposed on this 3 Hz current intensity "wave" for 60 seconds followed by a current intensity modulated as a 40 Hz triangle wave between a CIW of 15 and 25 microamperes with an AC frequency of 116 Hz sine wave superimposed on this current intensity wave for 30 seconds, etc.

Another example of a variation is by lowering the intensity of the output current to a range that changed according to the variability scheme of the programming to be below 1 milliamp and increasing the duration of the use of the device to a longer total treatment time. Such a configured device can be worn continuously over many hours with a current intensity setting that is below the point of concern for the user or below the point that significant sensation can be felt or muscular stimulation could occur. By increasing treatment time while decreasing, but varying the intensity of the output current in a waveform-like fashion simultaneously with other output characteristics such as AC frequency, etc., beneficial treatment results were able to be obtained more quickly than with traditional devices.

Various embodiments described have been experimentally shown to minimize treatment plateaus, accommodation, habituation or tachyphylaxis.

Another example of a variation is by using a multi-channel device whereby the intensity of the output current is modulated in a waveform-like fashion and can be synchronized or desynchronized between the various channels while keeping the AC frequency and/or DC current treatment packets constant (e.g. 3 Hertz on channel A and 3 Hertz on channel B) or systematically varying (e.g. 3 Hertz on channel A and 116 Hertz on channel B) and/or by varying systematically or randomizing the synchronization or desynchronization or both over a period of output time.

Another example of a variation is to systematically and/or randomly or both, continuously change all the parameters of output. A software-encoded algorithm is anticipated to direct the output in this manner.

Another example of a variation is being able to sweep through various intensity output current conditions either in an increasing sweep or decreasing sweep (e.g. sweeping from 0-100 uA, then 90-60 uA, then 25-75 uA, then 30-15 uA, etc. over a period of time) while the AC/DC frequency function is sweeping through various frequencies (e.g. 1-1, 000 Hz, then 1-3 Hz, then 40-100 Hz, etc.) over the same or different period of time. As another example, is sweeping between any two intensity amplitude modulation values, either broad values or small, such as ascending from "min" to "max" uA (intensity window) at an ascending sweep amplitude modulation between "min"-"max" Hz in a specified time envelope, or descending from "max"-"min" Hz in a specified time window, or the ability to sequentially alternate between ascending and descending amplitude modulations in a specified time envelope. Each of these sweeps may be tailored as a specific sequence that targets a particular biological structure, or to provide a particular function. Or, to sweep between any two frequencies, either a broad sweep window, such as ascending from 0-10 MHz, or descending from 10 MHz-0, or sequentially alternate between ascending and descending frequency sweeps in a specified time envelope. Additionally, the ability to descend, ascend, or sequentially alternate in a small sweep window, such as 20 Hz to 30 Hz in a specified time envelope. The ability to develop specific sequences that target particular biological structures and functions. Numbers are provided as examples only and are not intended to limit the ability of the application of the method.

Another example of a variation is to have the "Duty cycle" pulsed. Another example is where the frequency and/or the amplitude modulation are representative of the Fibonacci progression and/or the Golden Ratio (approximately 1.618 . . . ).

As apparent from the above embodiments, it is believed the modulation of electrical current intensity (either user controlled or non-user controlled), and/or systematically varying (waveform-like modulation), and/or with DC positive and/or negative current level, and/or in combination with other electrical output parameters such as AC frequency modulation are new to at least the field of TENS devices. Further, experiments with the above embodiments have shown increased efficacy on the healing of equine, canine and human tissues and physiologic functions beyond the pain blocking effects produced by prior art TENS devices.

Accordingly, the use of this new electrotherapeutic technique is foreseen to have beneficial effects on human, veterinary, plant and other biological tissues and physiologic functions in vivo and in vitro that are not able to be attained by modulation of the other output parameters alone, such as found in the prior art methods of manually adjusting and modulating intensity, frequency, frequency sequences, frequency combinations in dual channel devices, polarity, duty cycle, waveform, single or multiple channel devices, interferential devices, etc.

Various embodiments in consideration of the new signal manipulation scheme is contemplated for use in traditional TENS/MENS applications. For example, one embodiment demonstrates an On/Off switch user activated miniaturized human and veterinary TENS/MENS/Iontophoresis device, with non-user controlled microcurrent output that delivers a preprogrammed waveform modulated intensity function with other output parameters superimposed on the modulated intensity. Another embodiment discloses the manipulation and modulation of the electrical current intensity both singly and in combination with systematic and/or random modulation of the other output parameters, such as frequency, frequency sequences, duty cycle, waveform, sweeps, polarity, single or multiple channel outputs, interferential, etc. for human and veterinary electro-therapy systems such as TENS/MENS/Iontophoresis, as well as in vitro plant and/or animal cellular culture systems and cellular electroporation.

One embodiment allows a user to place a self-powered electrode(s) on the skin like a large band-aid, and connect a single channel device wirelessly to the self-powered electrode. The user can turn it on and let the program run until the user turns the device off.

With the non-supervisory, self-contained system, therapy can be implemented while conducting activities, for example, household chores, or while sleeping, thus saving a great deal of time going to doctors to receive therapy. This also allows for longer electro-therapy treatment durations with improved effectiveness.

By reducing the various aspects of several different embodiments to practice and conducting animal experiments on horses, dogs, as well as humans, it appears reasonably foreseeable that the ability to affect various tissues or organ function as well as various physiologic functions, such as tissue repair, perfusion, erythrocytic 2.3 diphosphoglycerate, nitric oxide induction, hormone modulation, anti-inflammation secondary to various sources (e.g., cytokines, trauma, neuropeptides, etc.), blood pressure, vascular condition, pain of many origins and sources, nausea, emesis, wounds, orthopedic, nerve function, mood or psychological condition, or other organ or tissue function such as: connective tissue matrix, heart function, penile or clitoral perfusion, kidney, liver, pancreas, bladder, prostate or any other viscera or gland, ocular, dental health, etc. over a number of days, weeks, months, years or decades.

Accordingly, one embodiment enables a user to treat an area of the skin and lower blood pressure and/or inflammatory markers with or without other medication over a period of time sufficient that treatment could influence the development of other cardio-vascular conditions. Another embodiment enables a user to electrically stimulate cell culture systems in vitro and obtain enhanced effects over the prior art methods. Another embodiment enables a user to electroporate compounds of interest into a group of cells in vitro and obtain enhanced effects over the prior art methods. Another embodiment enables a user to electrically extract botanical compounds of interest without damaging heat sensitive constituents of the plant base material.

TENS/MENS/Iontophoresis output controller (and anticipates a multi-channel device) that is activated by the only user control, an ON/OFF switch, that activates firmware (hardware components, microchip and software programming) and has its intensity output current controlled by this firmware and has its output frequencies very accurately controlled by the firmware and a quartz timer and current controlled by the firmware with or without a voltage regulator and is powered by a 3 volt coin battery.

This is not a complete list of embodiments and other variations are contemplated. One embodiment increases perfusion and/or nitric oxide in the skin among other physiological processes, therefore when used over larger areas of the skin, the skin can produce decreases in Blood Pressure, enough that over increased duration of usage one's risk of Heart Disease and other vascular conditions can be diminished. One embodiment increases perfusion and/or Nitric Oxide and/or decreases inflammatory cytokines and/or local scalp hair follicle cell induction and/or follicular stem cell induction and/or increased migration of stem cells among other physiological processes in the scalp can be utilized to stop or slow scalp hair loss and/or increase hair regrowth processes. One embodiment improves incontinence of urine and stool. One embodiment can decrease symptoms of nephritis, glomerulonephritis, pyleonephritis, etc. and slow progression. One embodiment can decrease symptoms of hepatitis, hepatomegaly, gall bladder pain and inflammation.

One embodiment can decrease symptoms of acute and/or chronic cystitis, interstitial cystitis or chronic non-infection related urethritis with a probe that is inserted vaginally. One embodiment improves healing of bladder distension after being overstretched from an obstruction or other bladder inflammation or dysfunction when used with a rectal probe connecting an electrode placed over the skin above the pubic bone. One embodiment improves hemorrhoids and rectal and anal fissures when used with a rectal probe connecting an electrode placed over the skin above the pubic bone. One embodiment can be used to minimize swelling and promote healing in acute trauma conditions, such as injuries and including head and spinal cord injuries. One embodiment can be used as an adjunct to treat acute, subacute or chronic Compartment Syndrome in a limb. One embodiment can decrease symptoms of thyroiditis, both local and systemic, both hyper and hypo-functioning types. One embodiment can decrease symptoms of laryngitis, particularly in overuse syndromes as with singers and orators. One embodiment can be used to improve treatment outcomes of ocular conditions such as, but not limited to macular degeneration and retinitis, diabetic opthalmoplegia and diabetic retinopathy. One embodiment can be for the treatment of the eye via electroconductive contact lens or electrodes applied above or around the eye. The application of the method can be useful for the treatment of ophthalmic conditions such as cataracts, diabetic retinopathy, macular degeneration, refractive errors, glaucoma, etc.

One embodiment can be used to affect and/or improve known effects of electrical stimulation applied to biological tissue being studied in vitro. It is anticipated that one embodiment can be applied to cell culture systems of any methodology and any cell type such as plant, human or veterinary tissue or any combination of these. One embodiment increases perfusion and/or nitric oxide in the pelvis among other physiological processes, therefore when used near the genitalia can increase sexual responsiveness in both men and women. One embodiment can decrease symptoms of ovarian cyst and/or folliculitis with electrodes placed on the abdomen or with a probe that is inserted vaginally. One embodiment is anticipated to decrease symptoms of pelvic cervical dysplasia, tonsillitis or other tissue inflammation associated with HPV infection. One embodiment is anticipated to decrease healing time of dermal, neural or mucosal irritations, lesions or wounds that are caused by various herpetic viruses. One embodiment, when combined with cellular electroporation techniques to drive compounds or other ingredients of interest across cell membranes and into cells is anticipated to improve methodology, enhance technique, and/or improve yields, and/or decrease cellular membrane damage and improve the results obtained with the methods taught in the prior art. One embodiment can decrease pain, physical discomfort and psychological symptoms of substance abuse withdrawal with transcerebral stimulation with the electrodes placed on the ear lobes, head, neck and/or abdomen. One embodiment can be used to beneficially affect the growth of algaes in aquariums, ponds and aquaculture. Another embodiment can be used to detrimentally affect the growth of algaes in aquariums, ponds and aquaculture or by altering the frequency, waveform positively affect the growth of fish in aquariums, ponds and aquaculture. One embodiment can be used to affect the growth of plants in hydroponic systems. One embodiment can be used to affect cellular telomeric attrition and telomerase expression in vivo and in vitro thereby affecting longevity of biological systems, tissues, humans and animals. Another embodiment can be used to in combination with cellular photosensors in vitro or in vivo to enable the tuning of the cells to influence specific cellular functions and behaviors such as biophoton emissions.

In another embodiment, the system can be used for spinal, intracranial treatment, etc. Also, as an implanted device(s) for anti-inflammatory, immunomodulatory, neuromodulatory, musculo-skeletal, visceral or other effects, either on its own or when combined with another implanted device's program. Also, as an opioid alternative, an exemplary system and/or method can use targeted waveforms modulation(s) to non-addictively activate opioid receptors and upregulate a body's opioid and endorphin systems for a bio-electronic medicine alternative to opioids. Conversely, as an opioid withdrawal alternative, targeted waveforms modulation(s) to non-addictively activate opioid receptors and upregulate the body's opioid and endorphin systems for a bio-electronic medicine alternative to drug detoxification and withdrawal.

"Smart electrodes" are envisioned to be used with the device such that some of the components of the device are split between the electrode and the driver device. The electrode and device will act as a "Lock and Key" system such that the device will not operate unless it recognizes specific components, some could be "dummy," some could be "nonsense," some could be active, some could be coded or encrypted in such a way that the electrodes engineered without these components will not work. These smart electrodes could have a microchip and/or other components attached to a PCB board or flex circuit built into the electrode in such as way as the device will not operate unless it recognizes these components and various codes on the smart electrode. The operating system could also be split between two "Lock and Key" microchips, one portion on the device and another on the electrode, thereby increasing the security that a compatibly engineered electrode was used with the device and impairing the ability of poorly engineered products to be substituted for use with the device.

Another embodiment of a Smart Electrode Lock and Key design is with an RFID built into the electrode with a coded signature that can communicate with the device and determines its authenticity thereby impairing the ability of poorly engineered products to be substituted for use with the device.

Other Smart Electrode embodiments are envisioned such as the "Smart PEMF" electrodes that has components such as microchips, mini-inductors, capacitors, magnetic chips, or a PEMF loop built into the electrode that, in combination with the device driver can sequentially fire discrete micro electromagnetic pulses that are geometrically shaped to produce a virtual "electron massage" effect.

Other Smart Electrode embodiments are envisioned such as one that has components built into the electrode that is programmed to be a sensor, reporting back to the driver device and providing a form of feedback loop to adjust the output according to the information collected. The program could sense when the electrode is worn out and send a signal to an indicator so that therapy is not attempted with an electrode that is no longer usable.

Another smart electrode embodiment is envisioned with specific design patterns layered into the electroconductive portion of the electrode as a technique to influence the spatial shaping of the electrical current flow as well as the mixing of currents in multi-channel systems.

Another electrode embodiment is envisioned with different materials for inclusion in the electroconductive hydrogel component of the electrode. For instance, by adding colloidal silver at about 25 ppm or more the hydrogel material will be rendered bacteriostatic, thereby decreasing the likelihood that the patient would get a dermal infection or cross-contaminate someone else handling the product. This is important for wound care, skin care and other infection treatment products such as shingles treatment electrodes. A good example of a beneficial application of this technology to equine electrodes would be ringworm. One horse with Ringworm can spread the infection throughout the entire barn. If you use the same electrode on different horses, you could cross-contaminate, so a colloidal silver impregnated gel electrode could have some protective benefits especially in the dirty barn setting. Plus the silver would likely facilitate conduction through the hydrogel improving electrode performance. Studies have shown an average of 13% of equine veterinary personnel are colonized with primarily the equine related genotype of Methacillin Resistant *Staphylococcus Aureus* (MRSA). So anything that can prevent zoonotic transmission of germs to veterinary personnel or to other horses from handling electrodes would be a helpful improvement. At this level of concentration colloidal silver is typically hypoallergenic and much less toxic and caustic than other types of antimicrobial compounds.

Another electrode embodiment is envisioned with the layer above the hydrogel being composed of an photo-emitting electrosensitive material so that when the current was flowing the gel would glow thereby creating an indicator light. This gel could be inlaid in the outer edge so that the edge of the electrode glowed or backed on the whole electrode surface or discrete sections so that they glowed and with the electrode foam backing cut away in the design of company branding, The below matrix in Table 1 describes one possible "control" program for treatment. This is programmed as a sequence of discrete output events at a specific current intensity for a specific time duration, upon initiation. For this example, the program generates a CIW 15 uA-30 uA window and runs for 4 hours. 1,443 coded lines are called out, each line code segment calls for a 10 second output duration event, encapsulated in the 223 steps below. At the end of the 4 hour program the device cycles back to line 1 to repeat the program.

TABLE 1

| Frequency (Hz) | microAmps | Duration | Cum. Time |
|---|---|---|---|
| 1. DC+ | 15 | 1 min. | 1 min |
| 2. DC− | 25 | 1 | 2 |
| 3. DC+ | 20 | 1 | 3 |
| 4. DC− | 30 | 1 | 4 |
| 5. DC+ | 25 | 1 | 5 |
| 6. DC− | 20 | 1 | 6 |
| 7. DC+ | 30 | 1 | 7 |
| 8. DC− | 15 | 1 | 8 |
| 9. 3 | 15 | 1 | 9 |
| 10. 3 | 20 | 1 | 10 |
| 11. 3 | 25 | 1 | 11 |
| 12. 3 | 30 | 1 | 12 |
| 13. 970 | 15 | 1 | 13 |
| 14. 970 | 20 | 1 | 14 |
| 15. 970 | 25 | 1 | 15 |
| 16. 970 | 30 | 1 | 16 |
| 17. 40 | 15 | 2 | 18 |
| 18. 40 | 20 | 2 | 20 |
| 19. 40 | 25 | 2 | 22 |
| 20. 40 | 30 | 2 | 24 |
| 21. 9 | 15 | 1 | 25 |
| 22. 9 | 20 | 1 | 26 |
| 23. 9 | 25 | 1 | 27 |
| 24. 9 | 30 | 1 | 28 |
| 25. 284 | 15 | 1 | 29 |
| 26. 284 | 20 | 1 | 30 |
| 27. 284 | 25 | 1 | 31 |
| 28. 284 | 30 | 1 | 32 |
| 29. DC− | 15 | 1 | 33 |
| 30. DC− | 20 | 1 | 34 |
| 31. DC− | 25 | 1 | 35 |
| 32. DC− | 30 | 2 | 37 |
| 33. DC− | 25 | 1 | 38 |
| 34. DC− | 20 | 1 | 39 |
| 35. DC− | 15 | 1 | 40 |
| 36. 100 | 15 | 1 | 41 |
| 37. 100 | 20 | 1 | 42 |
| 38. 100 | 25 | 1 | 43 |
| 39. 100 | 30 | 1 | 44 |
| 40. 13 | 15 | 1 | 45 |
| 41. 13 | 20 | 1 | 46 |
| 42. 13 | 25 | 1 | 47 |
| 43. 13 | 30 | 1 | 48 |
| 44. 396 | 15 | 1 | 49 |
| 45. 396 | 20 | 1 | 50 |
| 46. 396 | 25 | 1 | 51 |
| 47. 396 | 30 | 1 | 52 |
| 48. 49 | 15 | 1 | 53 |
| 49. 49 | 20 | 1 | 54 |
| 50. 49 | 25 | 1 | 55 |
| 51. 49 | 30 | 1 | 56 |
| 52. 562 | 15 | 1 | 57 |
| 53. 562 | 20 | 1 | 58 |
| 54. 562 | 25 | 1 | 59 |
| 55. 562 | 30 | 1 | 60 |
| 56. 0 | 0 | 1 | 61 |
| 57. 142 | 15 | 1 | 62 |
| 58. 142 | 20 | 1 | 63 |
| 59. 142 | 25 | 1 | 64 |
| 60. 142 | 30 | 1 | 65 |
| 61. 321 | 15 | 1 | 66 |
| 62. 321 | 20 | 1 | 67 |
| 63. 321 | 25 | 1 | 68 |
| 64. 321 | 30 | 1 | 69 |

TABLE 1-continued

| Frequency (Hz) | microAmps | Duration | Cum. Time |
|---|---|---|---|
| 65. 3 | 15 | 1 | 70 |
| 66. 3 | 20 | 1 | 71 |
| 67. 3 | 25 | 1 | 72 |
| 68. 3 | 30 | 1 | 73 |
| 69. 81 | 15 | 1 | 74 |
| 70. 81 | 20 | 1 | 75 |
| 71. 81 | 25 | 1 | 76 |
| 72. 81 | 30 | 1 | 77 |
| 73. 189 | 15 | 1 | 78 |
| 74. 189 | 20 | 1 | 79 |
| 75. 189 | 25 | 1 | 80 |
| 76. 189 | 30 | 1 | 81 |
| 77. 29 | 15 | 1 | 82 |
| 78. 29 | 20 | 1 | 83 |
| 79. 29 | 25 | 1 | 84 |
| 80. 29 | 30 | 1 | 85 |
| 81. 389 | 15 | 1 | 86 |
| 82. 389 | 20 | 1 | 87 |
| 83. 389 | 25 | 1 | 88 |
| 84. 389 | 30 | 1 | 89 |
| 85. 40 | 15 | 2 | 91 |
| 86. 40 | 20 | 2 | 93 |
| 87. 40 | 25 | 2 | 95 |
| 88. 40 | 30 | 2 | 97 |
| 89. DC− | 15 | 1 | 98 |
| 90. DC− | 20 | 1 | 99 |
| 91. DC− | 25 | 1 | 100 |
| 92. DC− | 30 | 2 | 102 |
| 93. DC− | 25 | 1 | 103 |
| 94. DC− | 20 | 1 | 104 |
| 95. DC− | 15 | 1 | 105 |
| 96. 111 | 15 | 1 | 106 |
| 97. 111 | 20 | 1 | 107 |
| 98. 111 | 25 | 1 | 108 |
| 99. 111 | 30 | 1 | 109 |
| 100. 294 | 15 | 1 | 110 |
| 101. 294 | 20 | 1 | 111 |
| 102. 294 | 25 | 1 | 112 |
| 103. 294 | 30 | 1 | 113 |
| 104. 51 | 15 | 1 | 114 |
| 105. 51 | 20 | 1 | 115 |
| 106. 51 | 25 | 1 | 116 |
| 107. 51 | 30 | 1 | 117 |
| 108. 20 | 15 | 1 | 118 |
| 109. 20 | 20 | 1 | 119 |
| 110. 20 | 25 | 1 | 120 |
| 111. 20 | 30 | 1 | 121 |
| 112. OFF | 0 | 1 | 122 |
| 113. 3 | 15 | 1 | 123 |
| 114. 3 | 20 | 1 | 124 |
| 114. 3 | 25 | 1 | 125 |
| 116. 3 | 30 | 2 | 127 |
| 117. 3 | 25 | 1 | 128 |
| 118. 3 | 20 | 1 | 129 |
| 119. 3 | 15 | 1 | 130 |
| 120. 321 | 15 | 1 | 131 |
| 121. 321 | 20 | 1 | 132 |
| 122. 321 | 25 | 1 | 133 |
| 123. 321 | 30 | 1 | 134 |
| 124. 94 | 15 | 1 | 135 |
| 125. 94 | 20 | 1 | 136 |
| 126. 94 | 25 | 1 | 137 |
| 127. 94 | 30 | 1 | 138 |
| 128. 355 | 15 | 1 | 139 |
| 129. 355 | 20 | 1 | 140 |
| 130. 355 | 25 | 1 | 141 |
| 131. 355 | 30 | 1 | 142 |
| 132. 124 | 15 | 1 | 143 |
| 133. 124 | 20 | 1 | 144 |
| 134. 124 | 25 | 1 | 145 |
| 135. 124 | 30 | 1 | 146 |
| 136. 50 | 15 | 1 | 147 |
| 137. 50 | 20 | 1 | 148 |
| 138. 50 | 25 | 1 | 149 |
| 139. 50 | 30 | 1 | 150 |
| 140. DC− | 15 | 1 | 151 |
| 141. DC− | 20 | 1 | 152 |
| 142. DC− | 25 | 1 | 153 |

TABLE 1-continued

| Frequency (Hz) | microAmps | Duration | Cum. Time |
| --- | --- | --- | --- |
| 143. DC– | 30 | 2 | 155 |
| 144. DC– | 25 | 1 | 156 |
| 145. DC– | 20 | 1 | 157 |
| 146. DC– | 15 | 1 | 158 |
| 147. 40 | 15 | 2 | 160 |
| 148. 40 | 20 | 2 | 162 |
| 149. 40 | 25 | 2 | 163 |
| 150. 40 | 30 | 2 | 165 |
| 151. 415 | 15 | 1 | 166 |
| 152. 415 | 20 | 1 | 167 |
| 153. 415 | 25 | 1 | 168 |
| 154. 415 | 30 | 1 | 169 |
| 155. 77 | 15 | 1 | 170 |
| 156. 77 | 20 | 1 | 171 |
| 157. 77 | 25 | 1 | 172 |
| 158. 77 | 30 | 1 | 173 |
| 159. 18 | 15 | 1 | 174 |
| 160. 18 | 20 | 1 | 175 |
| 161. 18 | 25 | 1 | 176 |
| 162. 18 | 30 | 1 | 177 |
| 163. 245 | 15 | 1 | 178 |
| 164. 245 | 20 | 1 | 179 |
| 165. 245 | 25 | 1 | 180 |
| 166. 245 | 30 | 1 | 181 |
| 167. OFF | 0 | 1 | 182 |
| 168. 9 | 15 | 1 | 183 |
| 169. 9 | 20 | 1 | 184 |
| 170. 9 | 25 | 1 | 185 |
| 171. 9 | 30 | 2 | 187 |
| 172. 9 | 25 | 1 | 188 |
| 173. 9 | 20 | 1 | 189 |
| 174. 9 | 15 | 1 | 190 |
| 175. 91 | 15 | 1 | 191 |
| 176. 91 | 20 | 1 | 192 |
| 177. 91 | 25 | 1 | 193 |
| 178. 91 | 30 | 1 | 194 |
| 179. 157 | 15 | 1 | 195 |
| 180. 157 | 20 | 1 | 196 |
| 181. 157 | 25 | 1 | 197 |
| 182. 157 | 30 | 1 | 198 |
| 183. 30 | 15 | 1 | 199 |
| 184. 30 | 20 | 1 | 200 |
| 185. 30 | 25 | 1 | 201 |
| 186. 30 | 30 | 1 | 201 |
| 187. 116 | 15 | 1 | 202 |
| 188. 116 | 20 | 1 | 203 |
| 189. 116 | 25 | 1 | 204 |
| 190. 116 | 30 | 1 | 205 |
| 191. 50 | 15 | 1 | 206 |
| 192. 50 | 20 | 1 | 207 |
| 193. 50 | 25 | 1 | 208 |
| 194. 50 | 30 | 1 | 209 |
| 195. DC– | 15 | 1 | 210 |
| 196. DC– | 20 | 1 | 211 |
| 197. DC– | 25 | 1 | 212 |
| 198. DC– | 30 | 2 | 214 |
| 199. DC– | 25 | 1 | 215 |
| 200. DC– | 20 | 1 | 216 |
| 201. DC– | 15 | 1 | 217 |
| 202. 40 | 15 | 2 | 219 |
| 203. 40 | 20 | 2 | 221 |
| 204. 40 | 25 | 2 | 223 |
| 205. 40 | 30 | 2 | 225 |
| 206. 783 | 15 | 1 | 226 |
| 207. 783 | 20 | 1 | 227 |
| 208. 783 | 25 | 1 | 228 |
| 209. 783 | 30 | 1 | 229 |
| 210. 89 | 15 | 1 | 230 |
| 211. 89 | 20 | 1 | 231 |
| 212. 89 | 25 | 1 | 232 |
| 213. 89 | 30 | 1 | 233 |
| 214. 147 | 15 | 1 | 234 |
| 215. 147 | 20 | 1 | 235 |
| 216. 147 | 25 | 1 | 236 |
| 217. 147 | 30 | 1 | 237 |
| 218. 62 | 15 | 1 | 238 |
| 219. 62 | 20 | 1 | 239 |
| 220. 62 | 25 | 1 | 240 |
| 221. 62 | 30 | 1 | 241 |
| 222. OFF | 0 | 1 | 242 |
| 223. Return to Line 1 to repeat program. | | | |

Using a current profile scheme as shown above or a modification therefore, an embodiment increases perfusion and/or Nitric Oxide and/or decreases inflammatory cytokines and/or local scalp hair follicle cell induction and/or follicular stem cell induction and/or increased migration of stem cells among other physiological processes in the scalp can be utilized to stop or slow scalp hair loss and/or increase hair regrowth processes.

Testing was conducted on the inventor's receding hairline and examined by a cosmetic surgeon at monthly intervals for 3 months. One electrode 1.5"×5" was placed on the forehead, another identical electrode was placed on the nape of the neck, the device was connected between these two electrodes. The device was worn for 1-2 hours 3-4 times each week. The hair diameter and hair density at the temples bilaterally was found to improve during the 3 month period.

An average of 50% of hairs transplanted during hair transplant surgery do not survive the transplant and fall out within the first several days after the procedure. One embodiment decreases hair loss after hair replacement surgery by increasing perfusion and/or Nitric Oxide and/or decreasing pro-inflammatory cytokines and/or increasing ATP and/or collagen formation among other physiological processes in the scalp such as stimulating migration and/or differentiation induction and/or implantation of stem cells. Moreover, it is believed the exemplary process can be used to downregulate or otherwise influence epigenetic function, histone acetylation and deacetylation as well as DNA methylation. For example, this method, when applied to the skin, can be used to augment elastin and collagen formation by the skin and connective tissue matrix Testing was conducted on one hair transplant volunteer conducted by a cosmetic surgeon. One electrode 1.5"×5" was placed on the forehead, another identical electrode was placed on the nape of the neck, the device was connected between these two electrodes. The device was worn for 1-2 hours a day, 3-4 times each week for one month after the surgery. Upon follow-up the cosmetic surgeon noted that the scalp recovered after surgery in an accelerated fashion and hair transplant loss was much less than the normal amount.

One embodiment decreases swollen prostates in Benign Prostatic Hypertrophy (BPH) and decreases pain in Prostatitis when used with a rectal probe connected to a reference electrode placed over the skin above the pubic bone. This drives the current through the pelvic region through the prostate and bladder tissues.

Testing was conducted on one volunteer with BPH and Prostatitis. The prostate was examined by ultrasound over a follow-up period of 6 months. The prostatic volume decreased slightly and the subjective prostatic pain report decreased significantly.

One embodiment decreases skin roughness and improves cosmetic appearance of skin, and decreases the depth and breadth of wrinkles in the skin, improving cosmetic appearance of the skin.

Example: 58 year old male volunteer used the device one time for two hours on the right lateral orbital region and nothing on the left side of the face as a control. His face was examined by a cosmetic surgeon and the skin roughness, hydration, softness and general cosmetic appearance was estimated to be 50% improved when compared to the other side. Similarly, the device was used one time for two hours on the right lateral orbital rhytides or crow's feet wrinkles and nothing on the left side of the face as a control. His face was examined by a cosmetic surgeon and the depth and breadth of the wrinkles on the treated side of the face was estimated to be 50% improved when compared to the other side.

Another embodiment improves skin disease conditions such as psoriasis, dermatitis, eczema, acne, etc. as well as anticipates many others.

Example: 27 year old female volunteer with psoriasis of the elbows was treated once for 4 hours on one elbow. Skin roughness was significantly diminished compared to the other side. Subjective evaluation of the individual suggested the itching sensations were significantly diminished when compared with the other elbow.

One embodiment decreases dermal wound healing times by increasing perfusion and/or Nitric Oxide and/or decreasing pro-inflammatory cytokines and/or increasing granulation tissue formation, stimulating migration and/or differentiation induction and/or implantation of stem cells, ATP and collagen formation among other physiological processes of concern in wound healing.

Example: 65 year old quadriplegic volunteer with pressure sores was treated with the device for 4 hours daily for one week. The pressure sores resolved in a progressive and uncomplicated fashion.

One embodiment decreases pain and swelling by increasing perfusion and/or nitric oxide and/or decreasing pro-inflammatory cytokines and/or nerve secreted substances such as Substance P or Neuropeptide Y and by increasing ATP and collagen formation among other physiological processes in tissues of orthopedic and/or neurological concern.

Example: 75 year old female volunteer diagnosed with lumbar spinal stenosis and experiencing peri-lumbar swelling and pain used the device for 6 hours during the day. The swelling and discomfort diminished significantly every time the device was used over the area of concern.

One embodiment improves healing times as well as improved healing quality in various types of orthopedic pain conditions in mesenchymal tissues such as, but not limited to myalgia, myositis, fasciitis, tendonitis, bursitis and tenosynovitis, arthritis (rheumatoid and osteo-arthritis) and injuries such as strains, sprains, repair of microtraumas in fascia, periostitis and other tissues of orthopedic concern.

Example: 18 year old female volunteer who was 4 years status post broken lumbar spine. She was spending most of her day trying to find her way out of pain. She had failed numerous types of orthopedic pain injection treatments and physical therapy. She began using the device for several hours each day. Within two months she was pain free for the first time in 4 years.

One embodiment diminishes peripheral neuropathy regardless of cause such as diabetic, viral disease related (HIV, Hepatitis C, etc.), hypoperfusion, etc.

Example: 62 year old male volunteer positive for Hepatitis B and C for an estimated 40 years with mild peripheral neuropathy of both feet used the device on one foot for 4 hours daily for 3 days and reported moderately increased sensation in the treated foot while the untreated foot remained unchanged.

One embodiment improves canine veterinary orthopedic conditions such as injuries or hip dysplasia.

Example: 14 year old Terrier with low back arthritis and hip dysplasia had his coat trimmed from the dorsal lumbosacral area to facilitate contact of the electrodes to the skin of the region. The device was left adhered to the skin for 3 days and activated and deactivated at random intervals throughout the day and left on overnight. Significant improvement in the dog's personality and vitality were reported by the owner as well as improved ability to climb stairs and take walks.

One embodiment decreases symptoms of sinusitis and facial pain when used on the face.

Example: 62 year old male volunteer with chronic right sided maxillary sinusitis used the device over this area of his face for 3 hours three days in a row. He reported significant decrease in the pain symptoms with use of the device. An extension of this is the application of the method to the ear, nose and throat for purposes of treating conditions of these tissues, for example applied external to or internal to the sinus cavity for sinusitis or allergies, or internal the mouth for treatment of periodontitis.

One embodiment can decrease pain and stimulate healing of post-surgical dental, orthopedic, cosmetic or other surgical procedures.

Example: 53 year old male volunteer post triple hernia surgery placed a device on his abdomen for 8 hours daily for the first 3 weeks after the surgery. His recovery was extremely hastened by use of the device as he was able to move comfortably 5 weeks ahead of schedule.

One embodiment can stimulate healing of orthopedic fractures and non-healing unions in bone fractures.

Example: 60 year old female volunteer broke her large toe and was in acute pain. The device was applied to her toe and foot and resolved the pain while the device was active. The bone was able to knit and heal 2 weeks sooner than expected with regular use of the device.

One embodiment can be used to decrease symptoms and stimulate healing of hand tendon syndromes such as DeQuervain's and Dupuytrens's as well as Carpal Tunnel Syndrome.

Example: 48 year old female volunteer diagnosed with DeQuervain's tenosynovitis was the only person in her family that had not had surgery for the condition yet. She used the device for 3-4 hours daily for one month and has not needed surgery since.

One embodiment can be used to improve Iontophoresis results when combined with other topically applied ingredients such as analgesics, anti-inflammatories, anti-virals, as well as cosmetic and/or nutraceutical compounds of benefit. The iontophoresis embodiment increases depth of penetration of the therapeutic substances over the prior art.

Example: 1 mL of Dexamethasone sodium phosphate (4 mg/ml) was placed under one side of the electrode, while 1 mL Sarapin was placed on the other side. The device was activated and treatment of chondromalasia of the fetlock joint in a 2 year old Thoroughbred racehorse in training was initiated. Severe swelling of the ankle and lameness was resolved in one treatment.

One embodiment can be used as an adjuvant to fermentation systems to influence the activity of the microbes of the ferment, such as a stalled ferment and/or influence the production of fermentation by-products of interest. One embodiment has been used with kefir, beer, wine, and mead ferments and was found to be satisfactory for this purpose.

Example: Extensive experimentation was conducted with non-dairy kefir culture grains over a period of a year that determined that biomass yields could be increased by 5-20% over controls when specific types of electrostimulation were utilized.

One embodiment can improve treatment outcomes over the prior art and decrease symptoms of Premenstrual Syndrome (PMS) with electrodes placed on the abdomen and/or lower back or with a probe that is inserted vaginally or rectally and the reference electrode placed on the abdomen.

Example: 35 year old female volunteer with chronic PMS placed the device over her abdomen when she began experiencing her PMS symptoms. She used the device once daily for 4 hours and was able to control her pain, cramping and dysphoria typical during her period.

One embodiment can decrease psychological symptoms of dysregulated mood such as depression, anxiety and/or insomnia with transcerebral stimulation with the electrodes placed on the ear lobes, head, neck and/or abdomen.

Example: A device was programmed with low frequencies and placed on the abdomen of a 58 year old male volunteer insomniac. He was able to get to sleep and stay asleep with the device running while attached to his abdomen.

One embodiment can be used to augment ionic aqueous and/or solvent (e.g. ethanol, hexane, etc.) extraction systems for plant materials and other phytochemicals, nucleic and ribonucleic acids, etc. without having to expose the botanical material to the potentially damaging effects of heat from hot water extraction. By increasing the current intensity to include either or both the microamperage (1-1,000 uA) and millamperage range (1-1,000 mA) One embodiment has been reduced to practice for commercial "cold" green tea extraction and was found to be more than satisfactory for this purpose.

Example: Extensive experimentation was conducted with pilot scale cold temperature green tea extraction. The process worked quite well and extracted the green tea constituents adequately when compared to hot water extraction methods without damaging the heat sensitive polyphenols or aromatic compounds.

One embodiment can be used to treat acute, subacute or chronic plantar fasciitis.

Example: 60 year old female volunteer with chronic plantar fasciitis, unable to run, her primary form of exercise. Using the device 4 hours daily for three weeks allowed her to return to running without pain.

Other embodiments contemplate the application of the method to the head, ears, transcranially, or to specific nerves such as the vagus nerve, to affect psychological aspects of brain function such as mood, physiological aspects of brain function such as sleep, and cognitive aspects of brain function such as attention, concentration, speed of mental processing, executive functions, facilitated learning, etc. This form of application of the method and device can also be applied to neurological and neuropsychological deficits such as ADD, learning deficits, traumatic brain injury, epilepsy, post-neurosurgical recovery, etc. Another possible application is to the feet via a device embedded into a shoe insole with or without electroconductive socks or stockings. This method of application can be used for general or non-specific purposes such as fatigue from standing, or applied for the treatment of specific conditions of the foot such as plantar fasciitis, arthritis, tendonitis, etc. Explicitly understood is that this method may aid in vitro or in vivo conditions, in anti-inflammatory effects. Additionally, the method can be used to produce an immunomodulation effect. For example, to affect cytokine expression, Th1 to Th2 immune expression, immune complement system, etc. This application can also produce anti-viral type effects as in, but not limited to, Herpes zoster (Shingles), post-Herpetic neuralgias as well as other bacterial and mycotic infections.

Accordingly, as will be appreciated by one skilled in the art, the present disclosure and of the microcontroller/microprocessor described herein may be embodied as an apparatus that incorporates some software components. Accordingly, some embodiments of the present disclosure, or portions thereof, may combine one or more hardware components such as microprocessors, microcontrollers, or digital sequential logic, etc., such as processor with one or more software components (e.g., program code, firmware, resident software, micro-code, etc.) stored as non-transitory signals or instructions in a computer-readable memory device such as a computer readable memory device or computer media, that in combination form a specifically configured apparatus that performs the functions as described herein. These combinations that form specially-programmed devices may be generally referred to herein "modules". The software component portions of the modules may be written in any computer language and may be a portion of a monolithic code base, or may be developed in more discrete code portions such as is typical in object-oriented computer languages. In addition, the modules may be distributed across a plurality of computer platforms, servers, terminals, and the like. A given module may even be implemented such that the described functions are performed by separate processors and/or computing hardware platforms.

In general, it should be understood that the circuits described herein may be implemented in hardware using integrated circuit development technologies, or via some other methods, or the combination of hardware and software objects could be ordered, parameterized, and connected in a software environment to implement different functions described herein. For example, the present application may be implemented using a general purpose or dedicated processor running a software application with non-transitory signals through volatile or non-volatile memory. Also, the hardware objects could communicate using electrical signals, with states of the signals representing different data.

It should be further understood that this and other arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

Further, although process steps, algorithms or the like may be described in a sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A method to therapeutically aid tissue or biological material via direct application of a mixed electrical signal, comprising:
   placing at least one or more electrodes in contact with at least one of a subject tissue, biological material, and biological containing environment;
   initiating a triggering of the mixed electrical signal;
   automatically applying, via processor control, a frequency dependent mixed electrical signal through the one or more electrodes, wherein the mixed electrical signal is a combination of at least two different frequency signals, a first frequency signal having a first minimum and maximum microamp range and a second frequency signal having a different second minimum and maximum microamp range, wherein a higher of the two frequency signals is superimposed on the lower peak amplitude of the two different frequency signals, whereby a current intensity window is sustained as an envelope along a profile of the lower of the two different frequency signals; and
   maintaining the application of the mixed electrical signal for a pre-determined period of time and varying at least one of the mixed electrical signal's amplitude, duration and frequencies according to a programmed schedule.

2. The method according to claim 1, further comprising adding a fixed or varying DC offset to the mixed electrical signal, wherein the DC offset can be positive or negative in value.

3. The method of claim 1, wherein the electrodes are connected to an electrode pad.

4. The method of claim 3, wherein the pad is disposable.

5. The method of claim 1, wherein at least one of a peak amplitude and a frequency of the first frequency signal is varied.

6. The method of claim 1, wherein at least one of a peak amplitude and a frequency of the second frequency signal is varied.

7. The method of claim 6, wherein at least one of a peak amplitude and a frequency of the first frequency signal is varied.

8. The method of claim 1, wherein the electrodes are configured to be placed subcutaneous to the subject tissue.

9. The method of claim 1, further comprising, generating at least one of spinal, intracranial, anti-inflammatory, immunomodulatory, neuromodulatory, musculo-skeletal, and visceral effects.

10. The method of claim 1, further comprising, activating or deactivating opioid receptors and up-down-regulate the opioid and endorphin systems as a bio-electronic medicine alternative to opioids or drug withdrawal.

11. The method of claim 1, further comprising applying the electrodes to multi-well cell culture plates, wherein at least one of a microbiological, plant and animal cell is in the plates.

12. The method of claim 1, further comprising, altering at least one of epigenetic function, histone acetylation, histone deacetylation, DNA methylation, elastin formation, collagen formation, and connective tissue growth.

13. The method of claim 1, further comprising, altering at least one of external cell membrane receptor(s), nuclear cell membrane receptor(s), agonist, antagonist, inverse agonist, calcium ion transport, sodium ion transport, and potassium ion transport.

14. The method of claim 1, further comprising, altering at least one of cell signaling, cell-to-cell communication, intracellular charge, extracellular charge, functioning of intracellular organelles, mitochondrial functioning, protein synthesis, phases of mitosis, interstitial fluid fields, and lymphatic functions in an in vitro or in vivo environment.

15. The method of claim 1, further comprising, altering at least one of disease process, infection, water consumption, microbiology, fertility, and nutrient uptake in a soil.

16. The method of claim 1, further comprising, altering at least one of a head, ear, transcranially, and specific nerves to affect aspects of brain function.

17. The method of claim 1, further comprising, altering at least one of an anti-inflammatory effect, immunomodulation effect, cytokine expression, Th1 to Th2 immune expression, immune complement system, anti-viral effects, and anti-bacterial effect.

18. The method of claim 1, further comprising, altering at least one of intravaginally, bladder, prostate, rectum, bone, organ, skin, limb, mouth, gum, sinus, ear, nose, and throat.

19. The method of claim 1, wherein contact of the electrodes to a subject tissue is via an ingestible pill having the electrodes therein, and treating at least one of irritable bowel syndrome, colitis, ulcerative colitis, gastroesophageal reflux disorder, diverticulitis, Crohn's disease, celiac disease, gallstone pain, gastroparesis, dysbiosis, food poisoning, diarrhea, and constipation.

20. The method of claim 1, further comprising, altering at least one of cellular electrophysiological feedback, cellular functions, cellular photosensors, and biophoton emissions.

* * * * *